United States Patent
Reider

(10) Patent No.: US 11,724,100 B2
(45) Date of Patent: Aug. 15, 2023

(54) REGULATED AND INTERACTIVE MUSCLE STIMULATION USING SENSORY REGULATED EMG TRIGGERED STIMULATION FOR FORGING NEURAL PATHWAYS

(71) Applicant: Brent C. Reider, Oxford, OH (US)

(72) Inventor: Brent C. Reider, Oxford, OH (US)

(*) Notice: Subject to any disclaimer, the term of this patent is extended or adjusted under 35 U.S.C. 154(b) by 93 days.

(21) Appl. No.: 17/097,884

(22) Filed: Nov. 13, 2020

(65) Prior Publication Data
US 2021/0060329 A1 Mar. 4, 2021

Related U.S. Application Data

(63) Continuation-in-part of application No. 16/839,105, filed on Apr. 3, 2020, which is a continuation-in-part of application No. 16/391,933, filed on Apr. 23, 2019, now Pat. No. 10,646,711, which is a
(Continued)

(51) Int. Cl.
*A61N 1/36* (2006.01)
*A61N 1/04* (2006.01)
*A61N 1/08* (2006.01)

(52) U.S. Cl.
CPC ......... *A61N 1/0452* (2013.01); *A61N 1/0456* (2013.01); *A61N 1/08* (2013.01); *A61N 1/36031* (2017.08)

(58) Field of Classification Search
CPC ............ A61N 1/36003; A61N 1/36007; A61N 1/36028; A61N 1/36031
See application file for complete search history.

(56) References Cited

U.S. PATENT DOCUMENTS

| 5,041,974 A | 8/1991 | Walker et al. |
| 5,800,501 A | 9/1998 | Sherlock |

(Continued)

OTHER PUBLICATIONS

Dhabhar, F. et al., Acute stress enhances while chronic stress suppresses cell-mediated immunity in vivo: a potential role for leukocyte trafficking, Brain, Behavior, and Immunity, 11, pp. 286-306, 1997.
(Continued)

*Primary Examiner* — George R Evanisko
(74) *Attorney, Agent, or Firm* — Standley Law Group LLP; Jeffrey Standley; Adam Smith

(57) ABSTRACT

Systems and methods for forging neural pathways in a user include stimulation and biofeedback devices in electronic communication with a controller. EMG regulated stimulation may be triggered by the controller or by detection of embodied sensory responses from said body inducted by the controller visually or with electrostimulation to induce stress to create a period of heightened plasticity for the user's brain and to induce muscular contractions consistent with a desired movement of a portion of the users' body. Images to create stress or of the desired movement may be provided at an electronic display. Biofeedback may be received, and where determined to be positive, continued or increased stimulation may be provided. Where the biofeedback is determined to be negative, the stimulation may be decreased or stopped. The controller may process embodied sensory input from the user to learn the patient's emotional and physical thresholds.

12 Claims, 16 Drawing Sheets

Related U.S. Application Data continuation-in-part of application No. 15/010,372, filed on Jan. 29, 2016, now Pat. No. 10,307,589.

(56) References Cited

U.S. PATENT DOCUMENTS

| | | | | |
|---|---|---|---|---|
| 5,913,310 | A * | 6/1999 | Brown | A61B 90/00 600/300 |
| D652,526 | S | 1/2012 | Peddicord | |
| D669,592 | S | 10/2012 | Peddicord | |
| D670,398 | S | 11/2012 | Peddicord | |
| D670,399 | S | 11/2012 | Peddicord | |
| D674,503 | S | 1/2013 | Peddicord | |
| 8,369,953 | B2 | 2/2013 | Peddicord | |
| 8,784,345 | B2 | 7/2014 | Peddicord | |
| 8,818,582 | B2 | 8/2014 | Peddicord | |
| D716,463 | S | 10/2014 | Peddicord | |
| RE45,585 | E | 6/2015 | Peddicord | |
| D739,545 | S | 9/2015 | Peddicord | |
| 9,173,806 | B1 | 11/2015 | Dematio et al. | |
| D754,870 | S | 4/2016 | Peddicord | |
| 9,372,533 | B1 | 6/2016 | Agrama | |
| RE46,163 | E | 9/2016 | Peddicord | |
| 9,655,808 | B2 | 3/2017 | Peddicord | |
| 10,307,589 | B2 | 6/2019 | Reider | |
| 10,646,711 | B2 | 5/2020 | Reider | |
| 2003/0180291 | A1 * | 9/2003 | Van Steveninck | A61K 41/17 435/6.12 |
| 2004/0171460 | A1 * | 9/2004 | Park | G16H 40/63 482/901 |
| 2010/0304864 | A1 | 12/2010 | Johnson et al. | |
| 2013/0066400 | A1 | 3/2013 | Perryman et al. | |
| 2013/0337975 | A1 | 12/2013 | Yanev et al. | |
| 2014/0057232 | A1 | 2/2014 | Wetmore et al. | |
| 2014/0200432 | A1 * | 7/2014 | Banerji | G16H 20/30 607/54 |
| 2014/0249602 | A1 | 9/2014 | Colborn | |
| 2017/0113015 | A1 | 4/2017 | Kaneko | |
| 2017/0216558 | A1 * | 8/2017 | Hughett | A61M 25/0017 |
| 2017/0216588 | A1 * | 8/2017 | Reider | A61N 1/36007 |
| 2017/0252264 | A1 | 9/2017 | Peddicord | |
| 2018/0168905 | A1 * | 6/2018 | Goodall | A61B 5/1124 |
| 2018/0333575 | A1 | 11/2018 | Bouton | |

OTHER PUBLICATIONS

Dopp, J. et al., Increased natural killer-cell mobilization and cytotoxicity during marital conflict, Brain, Behavior, and Immunity, 14, pp. 10-26, 2000.

Güntekin, B. et al., A review of brain oscillations in perception of faces and emotional pictures, Neuropsychologia, 2014, 58, pp. 33-51.

Wesp, R. et al., Gestures Maintain Spatial Imagery, the american journal of psychology, 2001, 114(4), pp. 591-600.

Laborie Medical Technologies, Pelvic Floor Therapy—Biofeedback and More: Conservative Treatment for Pelvic Floor Disorders, retrieved from website Dec. 9, 2015, www.laborie.com.

InControl Medical LLC, APEX—OTC Device for Treatment of Stress Continence, retrieved from website visited Mar. 27, 2019, https://www.incontrolmedical.com/products/apex/.

InControl Medical, LLC, ATTAIN—the Ultimate Solution to Bladder and Bowel Leakage, retrieved from website visited Mar. 27, 2019, https://www.incontrolmedical.com/attain/.

Elvie, Elvie Trainer, retrieved from website visited Mar. 29, 2019, https://www.elvie.com/shop/elvie-trainer.

InControl Medical, LLC, Intensity, OTC device for Female Sexual Health, retrieved from website visited Mar. 27, 2019, https://www.incontrolmedical.com/products/intensity/.

Han, J., Heroin Addicts Treated with Transcutaneous Electrical Nerve Stimulation of Identified Frequencies, Regulatory Peptidees, 1994, 54(1), pp. 115-116.

Reider, B., Medical Imaging Enfranchising the Patient for Better Feedback and Life-Long Wellness: From Female Pelvic Floor Control to Orgasm, Journal of Surgical Case Reports and Images, Mar. 8, 2020, pp. 1-8.

Schwarzer, C., 30 Years of Dynorphins—New Insights on Their Functions in Neuropsychiatric Diseases, Pharmacology & Therapeutics, 2010, 123(3), pp. 53-370.

Ullman, M., Contributions of Memory Circuits to Language: the Declaration/Procedural Model, Cognition, 2004, 92 (1-2), pp. 231-270.

Agre, P. et al., Pengi: an implementation of a theory of activity, the Proceedings of the sixth national conference on artificial intelligence, 1987, Seattle, WA: American Association for Artificial Intelligence, pp. 268-272.

Ahrens, L. et al., Impaired visuocortical discrimination learning of socially conditioned stimuli in social anxiety, Social cognitive and affective neuroscience, 2015, 10(7), pp. 929-937. https://doi.org/10.1093/scan/nsu140.

Baddeley, A., Working Memory, Science, 1992, 255, 5044, pp. 556-559. DOI: 10.1126/science.1736359.

Barsalou, L. et al.,Grounding conceptual knowledge in modality-specific systems, Trends in cognitive sciences, 2003, vol. 7 No.2.

Bower, J. et al., Cognitive processing, discovery of meaning, CD4 decline, and AIDS-related mortality among bereaved HIV-seropositive men, Journal of consulting and clinical psychology., 1998, 66: pp. 979-986.

Brooks, R., Intelligence without representation, Artificial Intelligence, 1991, 47, pp. 39-159.

Brooks, R., Intelligence without reason, Proceedings of 12th international joint conference on artificial intelligence, Sydney, Australia, 1991, pp. 569-595.

Cruz-Martin, A. et al., A dedicated circuit links direction selective retinal ganglion cells to primary visual cortex, Nature, 2014, 507, pp. 358-361.

De Voogd L. et al., Eye-movement intervention enhances extinction via amygdala deactivation, J. Neurosc., 2018, 38, pp. 8694-8706.

Defense Advanced Research Projects Agency (DARPA) (2013). DARPA and the Brain Initiative https://www.darpa.mil/program/our-research/darpa-and-the-brain-initiative.

Defense Advanced Research Projects Agency (DARPA) (2017). TNT Researchers set out to advance pace and effectiveness of cognitive skills training. https://www.darpa.mil/news-events/2017-04-26.

Egorova, N. et al., In the face of pain: the choice of visual cues in pain conditioning matters, European journal of pain (London, England), 2017, 21(7), pp. 243-1251, https://doi.org/10.1002/ejp.1024.

Ezequiel M. et al., The Role of Gestures in Spatial Working Memory and Speech, the American Journal of Psychology, 2004, 117(3), pp. 411-424, doi:10.2307/4149008.

Glenberg A. et al., Grounding language in action, Psychonomic Bulletin and Review, 2009, 9, pp. 558-565.

Goldman, B., The fearful eye, using virtual reality to hack fright. Standford Medicine, 2017, https://stanmed.stanford.edu/2017summer/huberman-virtual-reality-curing-fear-anxiety.html.

Heekyung, J. et al., An unbiased view of neural networks: more than meets the eye, Neuron., 2018, 100,5, pp. 1019-1021.

Huberman, A., The Joe Rogan Experience #1513—Andrew Huberman, Jul. 2020, https://www.youtube.com/watch?v=gLJowTOkZVo.

Kloppel, S. et al., Can Left-Handedness be Switched? Insights from an Early Switch of Handwriting, the journal of neuroscience, 2007, 27(29), pp. 7847-7853.

Kontula, O. et al., Determinants of female sexual orgasms, Socioaffective neuroscience & psychology, 6, 31624, 2016, https://doi.org/10.3402/snp.v6.31624.

Laumann, E. et al., Sexual dysfunction in the United States: prevalence and predictors, Journal of the American Medical Association, 1999,281(6), pp. 537-544. https://doi.org/10.1001/jama.281.6.537.

McCall, K. et al.,Cues resulting in desire for sexual activity in women, the journal of sexual medicine, 2006, 3(5), 838-852, https://doi.org/10.1111/j.1743-6109.2006.00301.x.

(56) References Cited

OTHER PUBLICATIONS

O'Regan, J. et al., A sensorimotor account of vision and visual consciousness, Behavioral and brain sciences, 2001, 25 (4), pp. 883-975.
Peterson, J. Maps of meaning: the architecture of belief, 1999, New York, NY: Routledge.
Quartz, S. et al., The neural basis of cognitive development: a constructivist manifesto, Behavioral and brain sciences, 1997, 20, pp. 537-596.
Rizzolatti, G. et al., The Mirror-Neuron System, Annual review of neuroscience, 2004, 27, pp. 169-192.
Rupert, R. Cognitive Systems and the Extended Mind, 2009, Minds & Machines, Oxford University Press.
Segerstrom, S. et al., Psychological stress and the human immune system: a meta-analytic study of 30 years of inquiry, Psychological bulletin, 2004, 130(4), pp. 601-630. https://doi.org/10.1037/0033-2909.130.4.601.-.
Shwariz, M., Robert Sapolsky discusses physiological effects of stress, Stanford Report, 2007, https://news.stanford.edu/news/2007/march7/sapolskysr-030707.html.
Simion, C. et al., Interrupting the cascade: Orienting contributes to decision making even in the absence of visual stimulation, Perception & psychophysics, 2007, 69(4), pp. 591-595. https://doi.org/10.3758/BF03193916.
Sridharan, D. et al., Does the Superior Colliculus Control Perceptual Sensitivity or Choice Bias during Attention? Evidence from a Multialternative Decision Framework, Journal of neuroscience, 2017, 37 (3), pp. 480-511; DOI: https://doi.org/10.1523/JNEUROSCI.4505-14.2017.
Wieser, M., et al., Mutual influences of pain and emotional face processing, Frontiers in psychology, 2014; 5:1160.
Williams, N. et al., Treatment of Orgasmic Dysfunction in Women, Globallibrary of women's medicine, (ISSN:1756-2228) 2008; DOI 10.3843/GLOWM.10432.
Wilson, M., The case for sensorimotor coding in working memory, Psychonomic bulletin and review, 2001, 9: pp. 44-57.
Huberman, A., Huberman Lab, Department of Neurobiology, Standford School of Medicine, Stanford University, Fairchild Science Building, http://www.hubermanlab.com.

\* cited by examiner

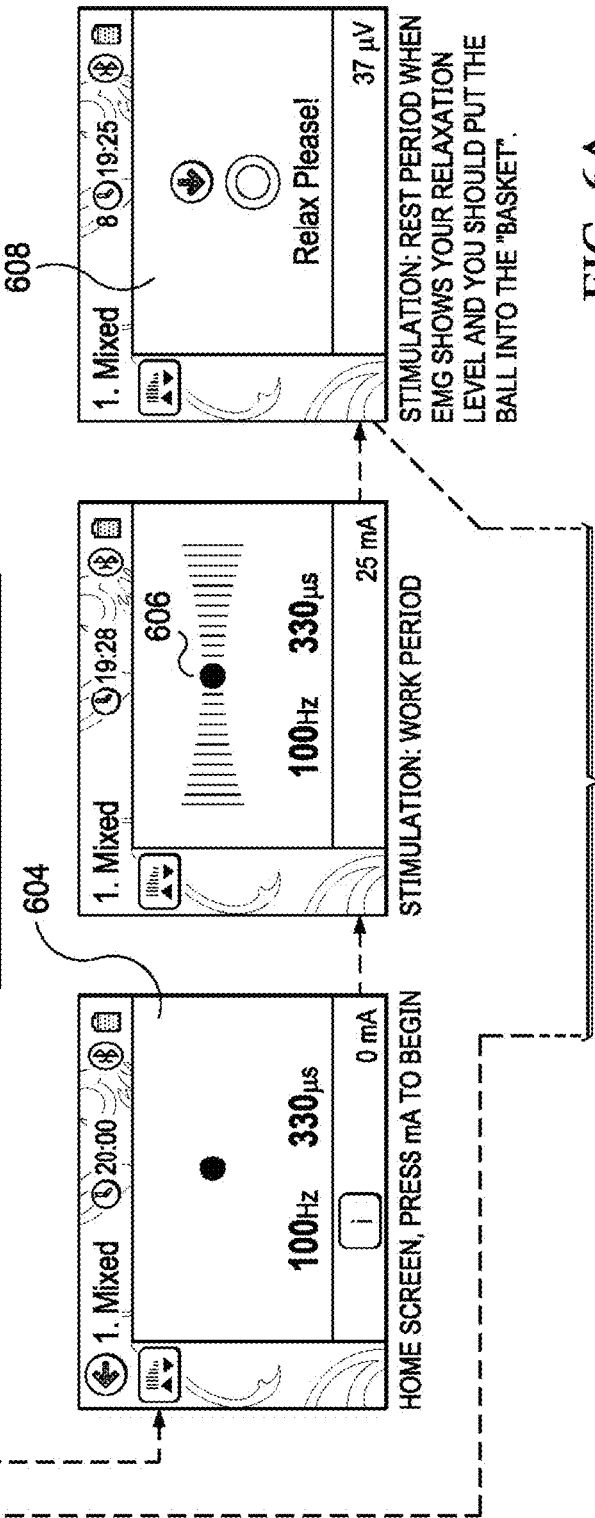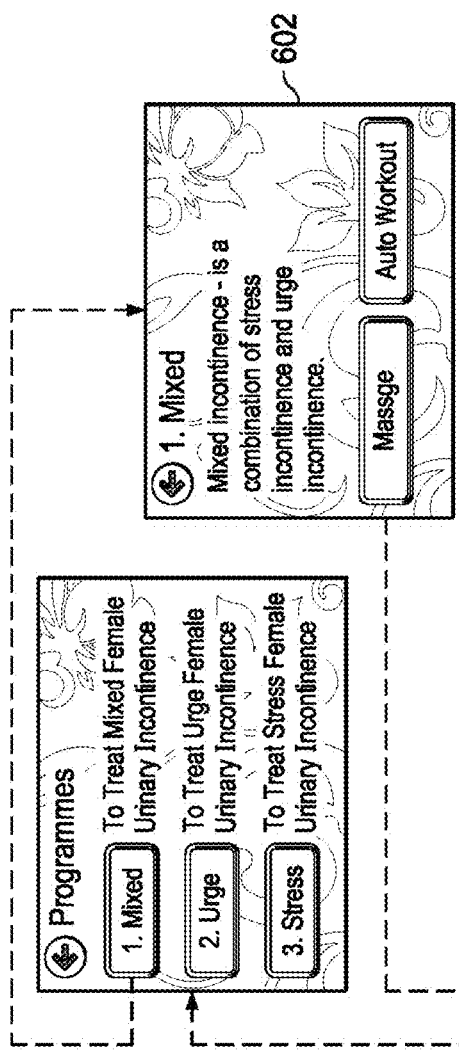

REGULATED AND INTERACTIVE MUSCLE STIMULATION USING SENSORY REGULATED EMG TRIGGERED STIMULATION FOR FORGING NEURAL PATHWAYS

CROSS-REFERENCE TO RELATED APPLICATIONS

This application is a continuation-in-part of U.S. Non-Provisional application Ser. No. 16/839,105 filed Apr. 3, 2020, which is a continuation-in-part of U.S. Non-Provisional application Ser. No. 16/391,933 filed Apr. 23, 2019, which is a continuation-in-part of U.S. Non-Provisional application Ser. No. 15/010,372 filed Jan. 29, 2016, the disclosures of each of which are hereby incorporated by reference in their entireties.

TECHNICAL FIELD

Exemplary embodiments of the present invention relate generally to systems and methods for providing regulated and interactive muscle stimulation using sensory regulated EMG triggered stimulation, such as for forging neural pathways.

BACKGROUND AND SUMMARY OF THE INVENTION

In human females, the pelvic floor muscles may become weak or lose conditioning as the result of age, childbirth, injury or disease. As a result, those with weak or unconditioned muscles may experience difficulty controlling or stopping the flow of urine. As a result, these individuals may experience episodes of incontinence, sexual dysfunction, or other undesirable situations related to muscle control. In order to improve the condition of the pelvic floor muscles and thus reduce the incidences of incontinence, improve sexual function, and/or improve other undesirable situations, individuals may perform various exercises including an exercise that involves the voluntary contraction of the pelvic floor muscles. The most well-known of these is the Kegel exercise. When performing Kegel exercises, a subject generally will attempt to contract their muscles for a short period of time, release the contraction of those muscles and then repeat this process. The desired result is the improvement of muscle tone in the pelvic floor muscles. Some individuals may have difficulty identifying the correct muscles to contract or may not hold the contraction long enough to be beneficial. In other cases, the individual may not remember to perform the exercises or lose interest and either stop performing the exercise or not perform them frequently enough to obtain a desired benefit.

There have been devices disclosed that assist a user in their efforts to learn to contract the muscles of the pelvic floor using various methods of electrically stimulating those muscles. In fact, various classes of muscle stimulators have been defined by the U.S. Food and Drug Administration including muscle stimulators for the improvement of muscle tone, muscle stimulators for the treatment of incontinence and stimulation for the treatment of muscle pain. Devices for facilitating some of these treatments are also known in the art. For example, U.S. Pat. No. 5,800,501 (Sherlock) discloses a device for providing an electrode for electrical stimulation. This same device may also be used to receive biofeedback signals. With such a device, a user may receive stimulation in order to strengthen the muscles of the pelvic floor. In addition to the stimulation portions, Sherlock also discloses a biofeedback portion. The biofeedback portion may be used to measure a user's muscle activity in response to such stimulation or as the result of exercises initiated by the user. Such a device may be of value to a user who desires to strengthen their pelvic floor muscles by combining stimulation with self-initiated muscle exercise. A user of such a device must be diligent with regard to their self-initiated exercises in order to see optimum results with regard to muscle strengthening. The use of games or similar methods of engaging a user may be beneficial in that such methods may encourage the user to persist in their exercise program. Various classes of muscle stimulators have been defined by the U.S. Food and Drug Administration including muscle stimulators for the improvement of muscle tone, muscle stimulators for the treatment of incontinence and stimulation for the treatment of muscle pain feedback.

Applications for regulated stimulation and interactive feedback extend beyond the pelvic floor muscles and incontinence issues. Various other muscle groups may be educated and re-educated to perform in desirable ways. Herein, the terms education and re-education may be used interchangeably. Examples of such applications include, but are not limited to, replantation patients, stroke victims, paralysis victims, and individuals experiencing other injuries or conditions. In such cases, the amount of muscle stimulation required for safe and optimal muscle education must be determined and utilized. In many cases, the optimal amount of muscle stimulation is specific to the particular user based on the user's physical characteristics, injury or condition, and progress within the muscle education program. Therefore, what is needed is a system and method which provides regulated muscle stimulation and interactive feedback for muscle education.

A system and method which provides regulated muscle stimulation and interactive feedback for muscle education is disclosed. The muscle education may involve neurological (hypothalamic) and spinal locomotor pattern generation. In an embodiment of such a device and system, a muscle stimulation system may be combined with a biofeedback receiving system that interacts with a plurality of games. A user of such a device may engage the muscle stimulation system to both provide conditioning to pelvic floor muscles and also to learn what sort of muscle response produces the desired conditioning of the pelvic floor muscles. A user may also use the plurality of games to encourage the user to perform exercises to strengthen the pelvic floor muscles. Games may have the benefit of encouraging the user to initiate the desired exercise and also to provide guidance to the user in regards to an optimum exercise level and technique. In an embodiment of the invention, a firewall may be created between the stimulation portion and the feedback portion to prevent the use of the feedback portion to control the stimulation. Such a firewall may be physical in nature, in other words, a physical isolation between the electronic components comprising the stimulation and biofeedback portion of an embodiment of the invention. In other embodiments of the invention, the firewall may be formed by the software programming of the embodiment. In such an example, the software may be designed to prevent interaction between the biofeedback and stimulation portions of the embodiment. In an embodiment of the device in which the firewall is formed in software, an enabling code may be implemented such that persons seeking to change or modify the device programming may be prevented from doing so without having the proper enabling code. Such an enabling code feature may also be used to prevent software modifications or game designs that may be harmful to a user of the device.

The muscle stimulation provided may be regulated to reflect a desired outcome. Too much muscle stimulation can be counter-productive as it may result in regression of muscle education. Too little muscle stimulation may not be sufficient to educate the muscles.

For each individual user the maximum therapeutic efficacy may be achieved by way of an algorithmic demonstration of sufficient muscle performance and respiration. Salient to the multi-variable algorithm is the status of the targeted muscle tissues including, but not limited to, muscle responsiveness to following the requisite task and a determination of blood flow. So, if the muscle is unable to perform specific template driven low level contraction challenges and/or exhibits any indications of spasm as monitored by EMG then the next stimulation (NMES) cycle is blocked and remains arrested for as long as the muscle or muscle group cannot perform the threshold point prequalification parameters. As such, the stimulation to be provided may be determined based on characteristics of the specific individual user.

Alternatively, or in addition, the stimulation to be provided may be determined based on the user's condition or injury. In exemplary embodiments, a visualization tool may be provided with the regulated stimulation. The visualization tool may provide a visualization of the desired outcome during periods of regulated stimulation to incorporate the user's locomotor pattern generation in therapy so as to include but not limit to procedural memory when the pattern of the objects drives action and when that perception is integral to action in the act of mapping the patterns of the world onto the patterns of the body. Alternatively, or in addition, the visualization tool may provide a visualization of the biofeedback received at the device for enhanced precision in developing specific procedural memory tasks for the specific individual user.

It is known that muscle stimulation can act as an analgesic for humans. It is known to provide TENS electrical stimulation to muscles as part of detoxification therapy, such as for humans who are detoxifying from smoked or intravenous, pure or black-market, heroin. However, patients may build tolerances to TENS therapy techniques. Further, patients often lose interest in non-interactive therapies. Therefore, what is needed is a regulated and interactive muscle stimulation for opioid detoxification therapy.

The present disclosures provide regulated and interactive muscle stimulation for opioid detoxification therapy. The regulated electrical impulses may be configured to mimic action potentials arriving from the central nervous system. The regulated muscle stimulation may be provided in synchronization with images displayed at an electronic display. Such images may be provided as part of a game. In exemplary embodiments, certain regulated muscle stimulations are provided to a particular muscle or muscle group to mimic a particular action potential arriving from the central nervous system. The patient may be monitored for biofeedback. The biofeedback may be in the form of electrical signals received from the muscle or muscle group due to muscle contractions, heart rate, muscle contractions and/or tension, blood flow, pain perception, blood pressure, some combination thereof, or the like. If the biofeedback meets certain parameters, a subsequent regulated muscle stimulation, different from the previously provided stimulation, may be provided. The stimulation provided may be consistent with stages of a therapy program. If the biofeedback does not meet certain parameters consistent with the given stage of the therapy program the user is at, further muscle stimulation may be arrested until the parameters are met. The user's success and failures in meeting the parameters may be reflected in the images displayed and/or the game progression. The muscle stimulation itself may act as an analgesic. Watching the images and/or participating in the game may occupy a significant amount of central nervous processing, distracting the user from pain or other unpleasant withdrawal symptoms.

Alternatively, or in addition, it is known that providing stimulation may induce neural plasticity. It is theorized that the releases of norepinephrine (a stress hormone and neurotransmitter) activates the immune system and causes alertness. Acetylcholine (a neurotransmitter) works in deep sleep and rest with norepinephrine to bring focus to synapsis of the brain to induce change. Vision and movement are also critical for inducing plasticity, forming new synaptic connections, and/or triggering production of certain neurotransmitters associated with plasticity. For example, mirror neurons may be activated by watching activity performed by others. As another example, spatial representations may be maintained in working memory by movement. What is needed is regulated and interactive muscle stimulation for forging neural pathways.

The present disclosures include systems and methods which provide regulated and interactive muscle stimulation for forging neural pathways. Regulated stimulation may be used to induce stress, thereby triggering the release of certain neurotransmitters which induce a period of heightened plasticity at a user's brain. The regulated stimulation may be followed by a muscle education program during the period of heightened plasticity. The muscle education program may utilize regulated muscle stimulation to induce desired movement. The muscle education program may include the synchronous display of visual cues to demonstrate desired movement.

The muscle education program may include the display of feedback from or regarding detected movements. These detected movements may include, for example without limitation, detect eye movements, facial expressions, and/or other muscle activity. Such muscle activity may be detected by, for example without limitation, transducers, cameras, infrared sensors, retina trackers, pupil trackers, facial recognition software image recognition software, moisture detectors, pressure sensors, heart rate monitors, blood pressure detectors, oxygen saturation sensors, respiration monitors, combinations thereof, or other biofeedback sensors. These features may assist in forging new neural pathways or otherwise reinforcing desired neural pathways during the period of heightened plasticity to improve retention and lasting change.

In exemplary embodiments, the feedback may include visually displayed simulations of the user's movement and/or sensory cues from the patient, including (but not limited to) eye and muscle movement to initiate regulated therapeutic stimulation to forge neuron pathways, such as but not limited to, in relation to the desired movement such that the user's progress towards one or more goals may be established. For example, without limitation, biofeedback from the user may be monitored to determine whether the user is in a positive state such as but not limited to experiencing relief, happiness, focus, or the like, or in a negative state such as but not limited to pain, anxiety, stress, combinations thereof, or the like. If the user is in a positive state, the stimulation may be continued or increased. If the user is in a negative state, the stimulation may be ceased or decreased.

In this way, the therapy may be advanced, but not beyond its efficacy. These features may assist in forging new neural pathways or otherwise reinforcing desired neural pathways, such as but not limited to during the period of heightened plasticity, to improve retention and lasting change.

Alternatively, or additionally, the feedback may include progress through one or more games. Such feedback may, at least in part, satisfy the user's desire for novelty, divert focus from pain or other undesirable sensations, or otherwise provide an enjoyable experience, thereby encouraging focus and progress. The feedback may, alternatively or additionally, provide progress towards one or more objective goals. As the user accomplishes these goals, the user's pleasure centers of the brain may be stimulated. In exemplary embodiments, the goals may be structured to provide the user with a realistic path for accomplishing the tangible objectives over time, which may provide users with a sense of satisfaction that moves the user towards overcoming physical and/or emotional injury. Such feedback may be provided intermittently and/or goals may be structured for intermittent accomplishment, such as in an unpredictable fashion.

The physical and/or electronic separation between the stimulation and biofeedback portions of devices used to provide the regulated stimulation and monitor for user muscle activity to provide feedback may provide safety against over stimulation, more accurate and precise stimulation, and more accurate and precise biofeedback.

Systems and methods for forging neural pathways in a user may include stimulation and biofeedback devices in electronic communication with a controller. Regulated stimulation, such as by EMG, may be triggered by the controller or where the controller detects embodied sensory responses from said body, which may be inducted by the controller visually or with electrostimulation to induce stress to create a period of heightened plasticity for the user's brain and to include muscular contractions consistent with a desired movement of said portion of the users body. Images to create stress or of the desired movement of said portion of the user's body may be provided at an electronic display. Biofeedback is received, and where determined to be positive, continued or increased stimulation is provided. Where the biofeedback is determined to be negative, the stimulation is decreased or stopped. During the entire therapy time the controller monitors and processes embodied sensory input from the patient to learn the patient's emotional and physical thresholds for effective and safe therapy. Indeed, processing speed of the control unit can be used to detect limits long before the patient.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 6 illustrates a legend for FIGS. 6A-C;

FIG. 6A are additional exemplary user interfaces;

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
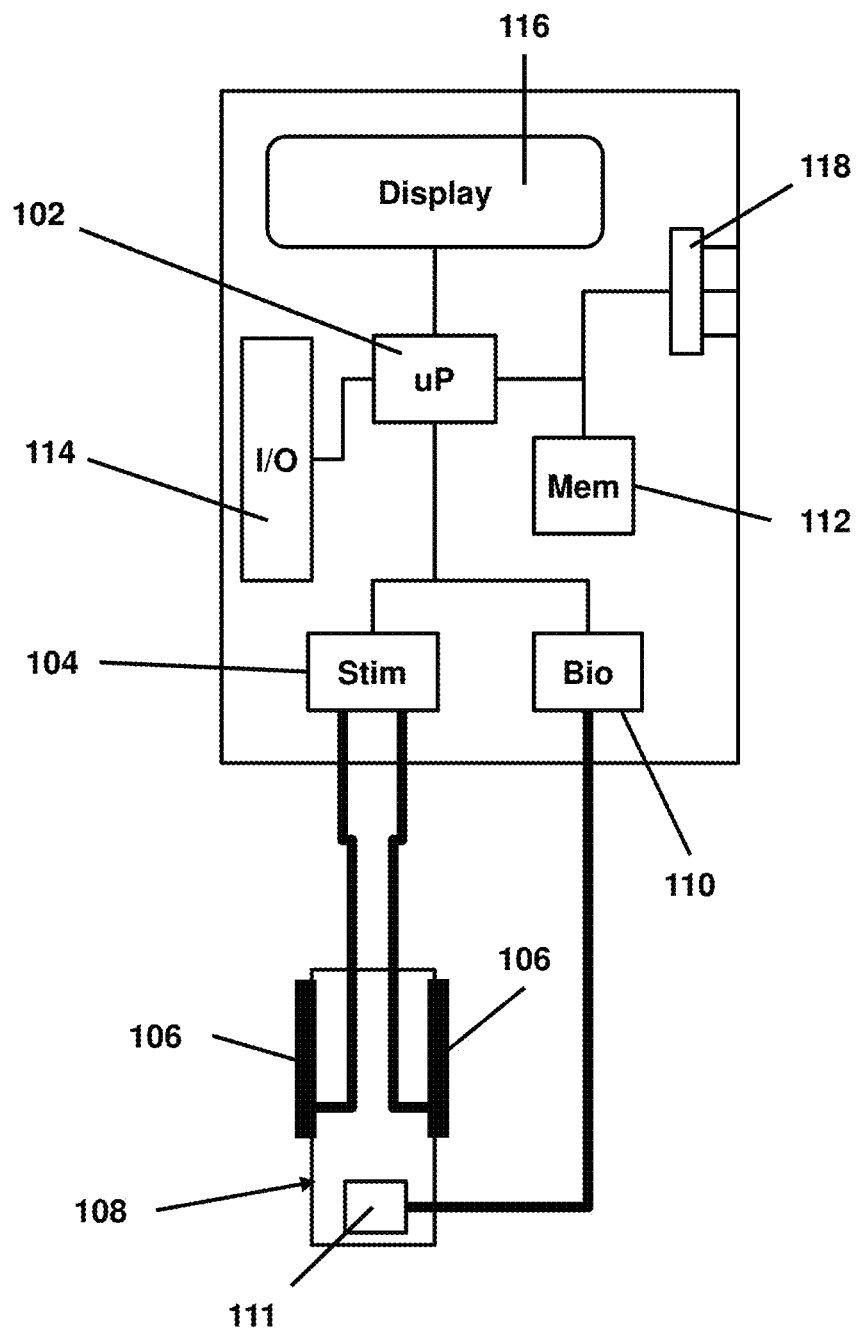
FIG. 1 is a simplified block diagram of an exemplary device.

Referring to FIG. 1, an embodiment of the invention may comprise a processor 102 that is in electronic communication with a stimulator 104. In such an embodiment the stimulator may be in electronic communication with a plurality of electrodes 106. In certain embodiments of the invention, these electrodes may be mounted to a probe device 108 that is configured to position the electrodes correctly when in use. In the illustrated embodiment, the processor 102 may also be in electronic communication with a biofeedback receiver 110. The biofeedback receiver may in turn be in electronic communication with a transducer 111. As shown, the transducer may be incorporated into the probe 108. Other embodiments may provide a transducer as a separate component to be used either in conjunction with the probe or separately when stimulation is not required. In embodiments of the invention, the transducer may be configured to receive electrical signals that are produced by the body when muscles contract. Other embodiments may use various pressure sensors to detect contraction of muscles against the transducer. Alternatively, or additionally to the transducers 111, other sensors may be utilized including, but not limited to, those configured to measure heart rate, muscle contraction and/or tension, blood flow, pain perception, blood pressure, some combination thereof, or the like.

As illustrated, the processor 102 may be in electrical communication with a memory 112, an input/output (I/O) section 114 which may comprise such inputs as pushbuttons, sound devices, or other selector devices and input/outputs such as Wi-Fi and other wired or wireless data connections, a display 116, and an external display interface 118. The external display interface may comprise wired and wireless connections to permit embodiments of the invention to communicate to external displays in order to enhance the user's interactions with the device.

Figure 2:
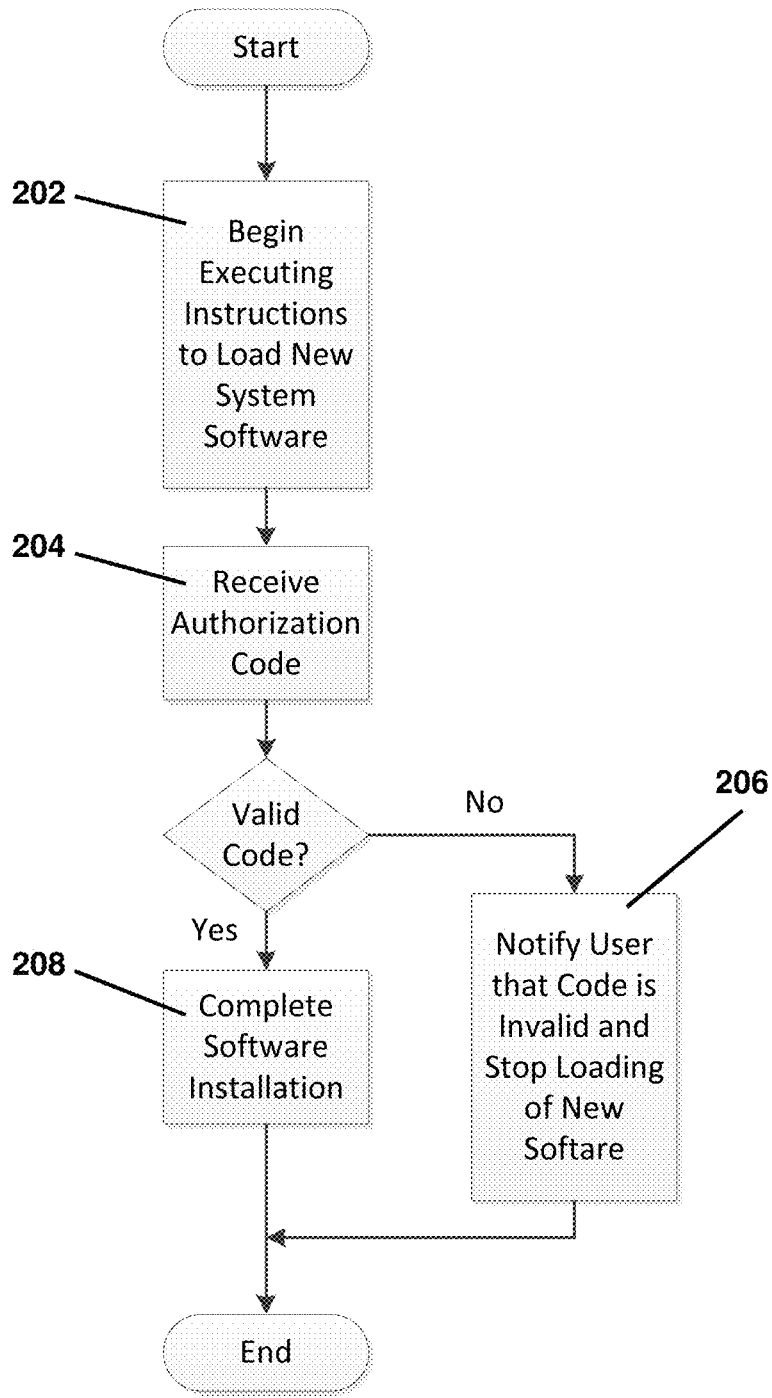
FIG. 2 is a flow chart of exemplary logic for authorizing re-programing of certain functions.

In embodiments of the invention, the memory 112 may be electronically programmable to permit the function of the device to be modified. Such programming may be done with the memory in place via a connection to the I/O section 114 or may be performed externally and written to a memory device that may then be physically inserted into the device such that the memory device is placed in electrical communication with the processor 102. In order to ensure device safety, in certain embodiments of the invention, an authorization code may be required to permit reprogramming of the operating software of the device. In an embodiment of the invention, a software update program may be executed by the processor 102 to cause the computer program controlling the operating parameters of the device to be amended. As illustrated in the flowchart of FIG. 2, if the software update program is executed 202, the program instructions may attempt to receive a programming authorization code 204. This receipt may be as the result of a prompt displayed on the display 116 or may be received as part of the process of receiving software instructions uploaded to the device for reprogramming. In order to determine if the programming authorization code is valid, an embodiment of the invention may compare the code to a list of predetermined codes stored in the memory 112 or may execute software instructions which comprise a predetermined code authorization algorithm. For example, an embodiment of the invention may receive a numerical value contained in a collection of software instructions which comprise a software update and apply a predetermined mathematical equation to that numerical value. If the received code does not match the result of the equation, the embodiment of the invention may determine the received code to be invalid. If the received code is invalid the device may notify the user and stop the reprogramming process 206. Alternatively, if the authorization code is valid, the software may begin the reprogramming process 208. As will be described in more detail later herein, embodiments of the invention may comprise interactive games that encourage a user to participate actively in the exercise process (referred to herein as true exercise). The code verification process illustrated in FIG. 2 may also be used to validate the installation of a new or updated interactive game. In such a manner, access to the stimulation portions of the invention may be closely regulated in order to prevent inappropriate or potentially harmful control of the stimulator 104 output section of the invention. Such a method may be used to safeguard a software isolation boundary formed (described in more detail later herein) between the stimulation and biofeedback portions of the invention.

In use, embodiments of the invention may utilize the stimulation section 104 in conjunction with the probe 108 and electrodes 106 to provide a stimulation signal to a user. As the result of the configuration of the probe 108 and control of the stimulation section 104 by the processor 102, a controlled stimulation signal may be output to a user. Such a signal may function to cause a specific set of the user's muscles to contract in a way that provides the necessary stimulation to improve the conditioning of those particular muscles. The level and duration of stimulation may be adjustable in certain embodiments of the invention. One function of the stimulation provided by the invention is to allow a user to experience the contraction sensation that may result in an optimum level of conditioning of a user's pelvic floor muscles. As such, the process of stimulation could be thought of as a process of training the user's muscles to perform a conditioning exercise necessary to further improve the conditioning and resulting performance of the user's muscles. As used in this description, the term "stimulation" has a different meaning than that of "exercise." As used herein, "exercise" or "true exercise" means the voluntary control by a person of certain muscles to provide a desired result whereas, stimulation means that the muscles are stimulated electrically to cause a contraction of the muscle. With regard to pelvic floor muscles, one of the desired results of various combinations of stimulation and exercise is an improvement in a person's ability to control the various muscles regulating the flow of urine.

A user may instruct an embodiment of the invention using an input/output device 114 such as a switch or pushbutton, to start the process of providing a stimulation signal. In embodiments of the invention, a user may be able to select a particular stimulation regimen. For example, a user may select the duration and intensity of the desired stimulation process. Embodiments of the invention may be provided with limitations and warnings to the user in the event that the level and duration of stimulation may exceed a level that is safe or may prove to be uncomfortable to a user.

Figure 3:
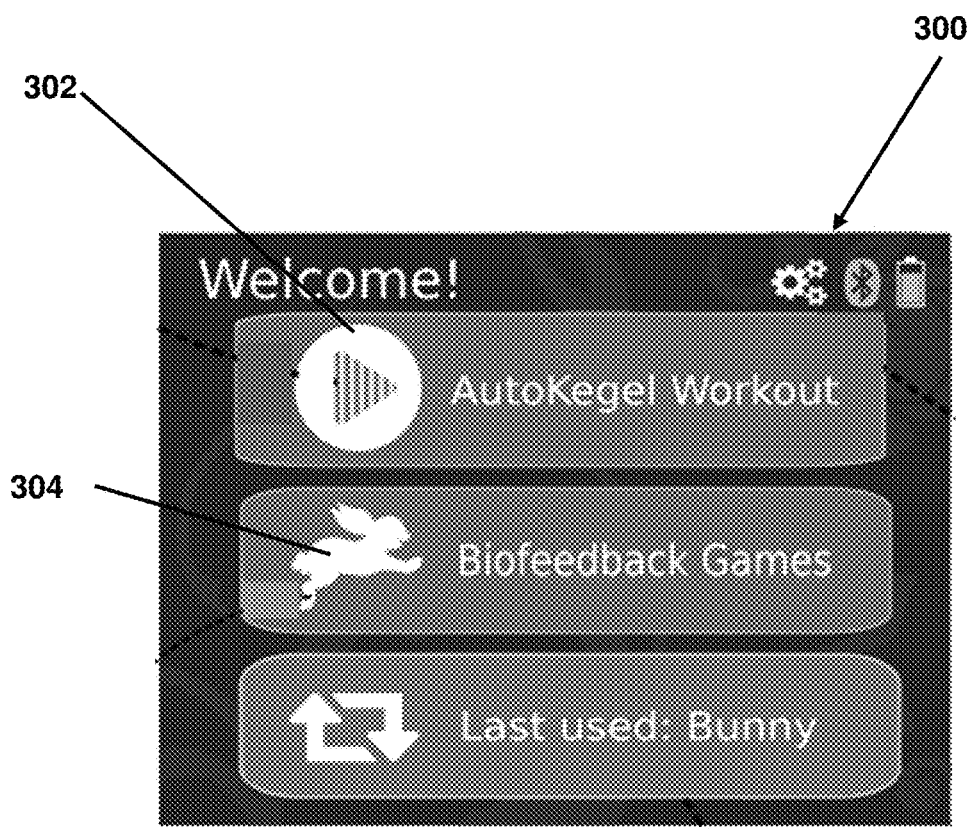
FIG. 3 is an exemplary user interface.
Figure 4:
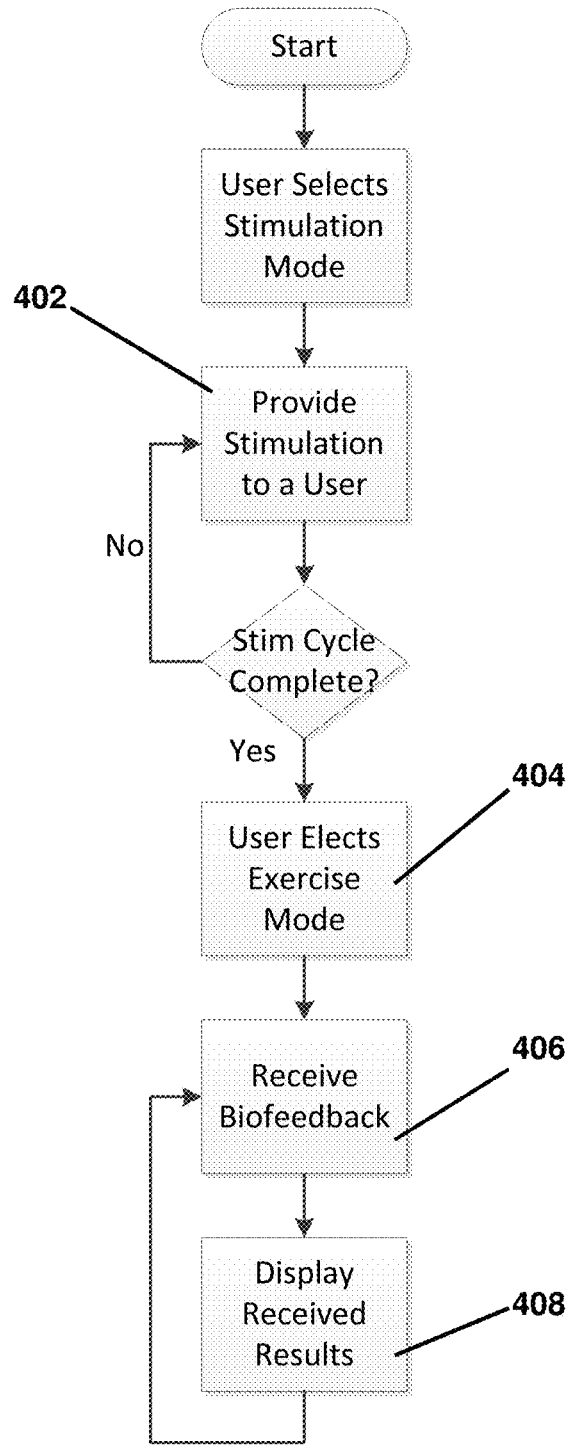
FIG. 4 is a flow chart of exemplary logic for operation of the device.
Figure 5:
FIG. 5 is another exemplary user interface for the device.
Figure 6B:
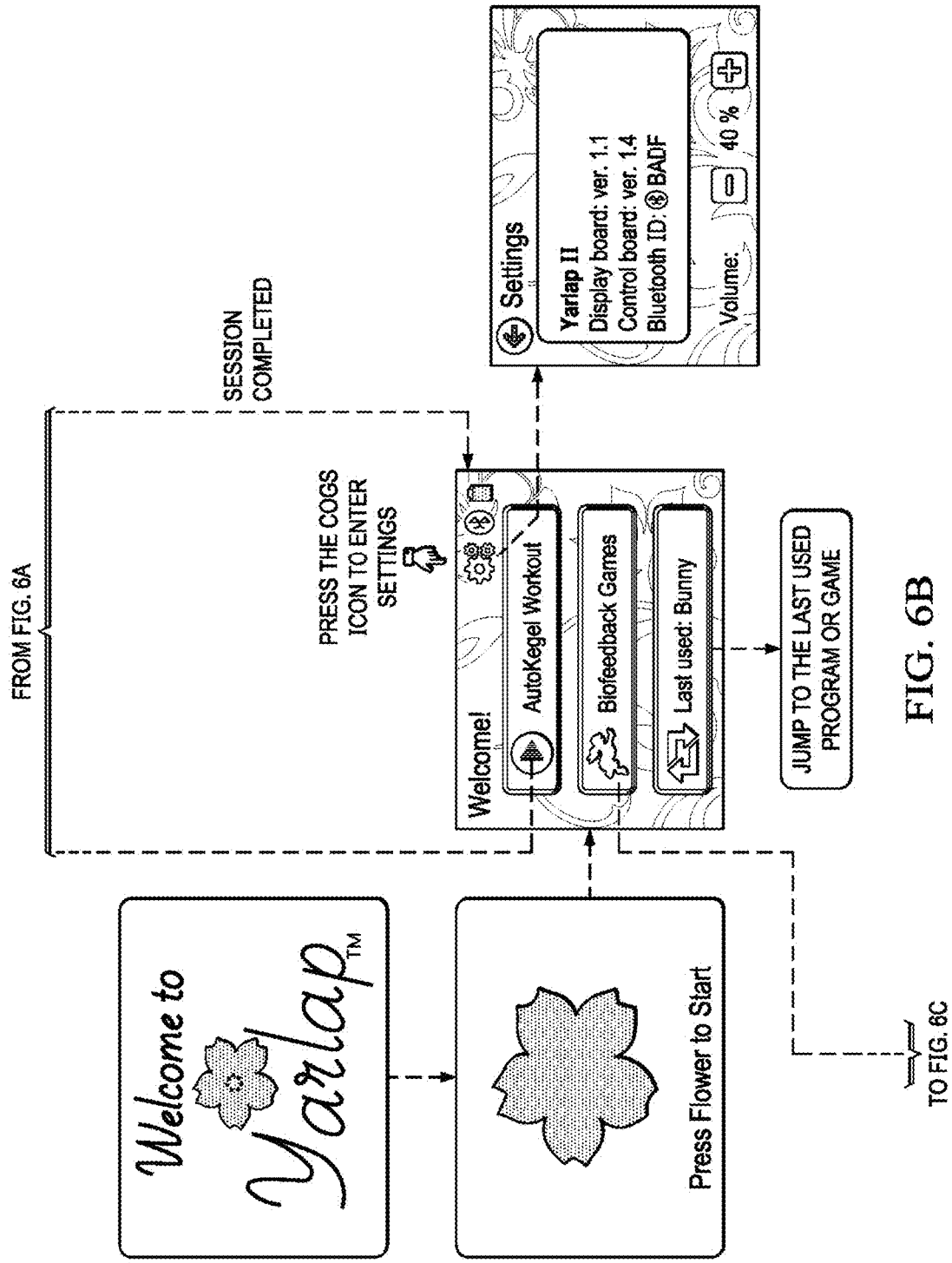
FIG. 6B are additional exemplary user interfaces.
Figure 6C:
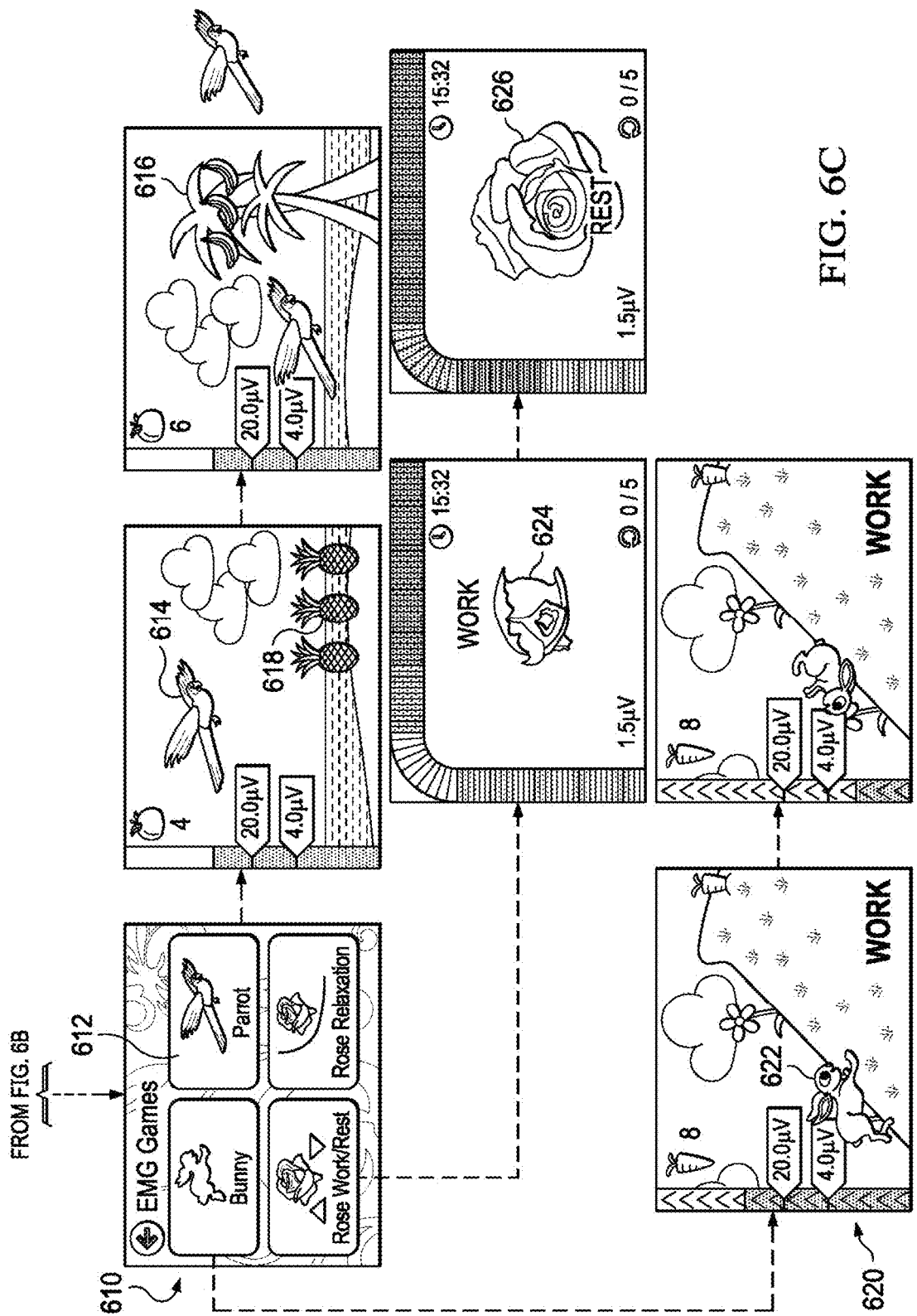
FIG. 6C are additional exemplary user interfaces.

In certain embodiments of the invention, a user may select between a stimulation mode and a biofeedback mode. An example of a user interface presenting such a selection is illustrated in FIG. 3. As is shown, a user may select stimulation 302 or biofeedback 304. As illustrated in the flow chart of FIG. 4, after a user selects stimulation from a menu similar to what is illustrated in FIG. 3, an embodiment of the invention may provide a stimulation signal to a user 402. When in such a mode, a user may be presented with a series of stimulation options. Referring to FIG. 5 which illustrates an example user interface, a user may be presented with menu 502 which provides options for various stimulation characteristics. For example, as illustrated a user may be presented with selections for the treatment of various types of female incontinence. As an example of how an embodiment of the invention may interact with a user, such a user may select a stimulation option from a main menu 300. When a user makes a menu selection, a second level of menu may be displayed 502. As illustrated, an embodiment of the invention may provide the user with additional choices in such a second level menu. Referring to FIG. 6 at 602, a user may select a massage stimulation option. When such an option is selected, a user may be presented with a user interface screen that displays the characteristics of the selected stimulation option 604. A user may elect to start the stimulation program corresponding to the selected option. When started, a user interface may provide feedback to the user in order to properly interact with the stimulation provided by the invention. For example, as illustrated, a user interface may provide an indication of the stimulation provided by the invention 606. In the illustrated example, a user may be required to relax their muscles during portions of the stimulation program. A user interface to provide the necessary feedback to a user is illustrated at 608. As illustrated, the stimulation signal may be removed and a user may be encouraged to relax their muscles to a certain level by a graphical illustration corresponding to a relaxed state. In the example shown, an indicator may be shown that moves across the user interface in response to a biofeedback input received by the invention that corresponds to a measured level of muscle relaxation. In such a manner, an embodiment of the invention may combine a stimulation portion 104 with a biofeedback portion 110. In exemplary embodiments, the stimulation portion 104 and/or electrodes 106 may be provided at a first probe or other device 108 and the biofeedback portion 110 and/or transducers 111 may be provided at a second probe or device 108. In such embodiments, the first and second probes or other devices 108 may be in electrical communication with one another or may be separate and in electrical communication with a common controller. The various devices 108 may be adapted to conform to or otherwise interact with specific muscle groups and/or body parts.

In embodiments of the invention in which there is an electrical connection between the stimulation and biofeedback portions of the electronic circuitry, allowing the biofeedback portion of the invention to control the stimulation output could potentially result in injury to a user. The capability for such an interaction should be carefully regulated to prevent potentially harmful unauthorized software modifications. In order to provide a level of protection to the user that prevents the stimulation portion of the invention from interacting with the biofeedback portion of the invention, a software "firewall" may be formed to prevent such an interaction. As was described earlier herein, a requirement that software changes require an authorization code in order to be implemented may provide an additional layer of protection in that an unauthorized programmer may be prevented from having the level of access necessary to reprogram the processor 102 to overcome the software firewall. In such a manner, an undesired interaction that could result from unauthorized programming may be prevented.

Figure 7:
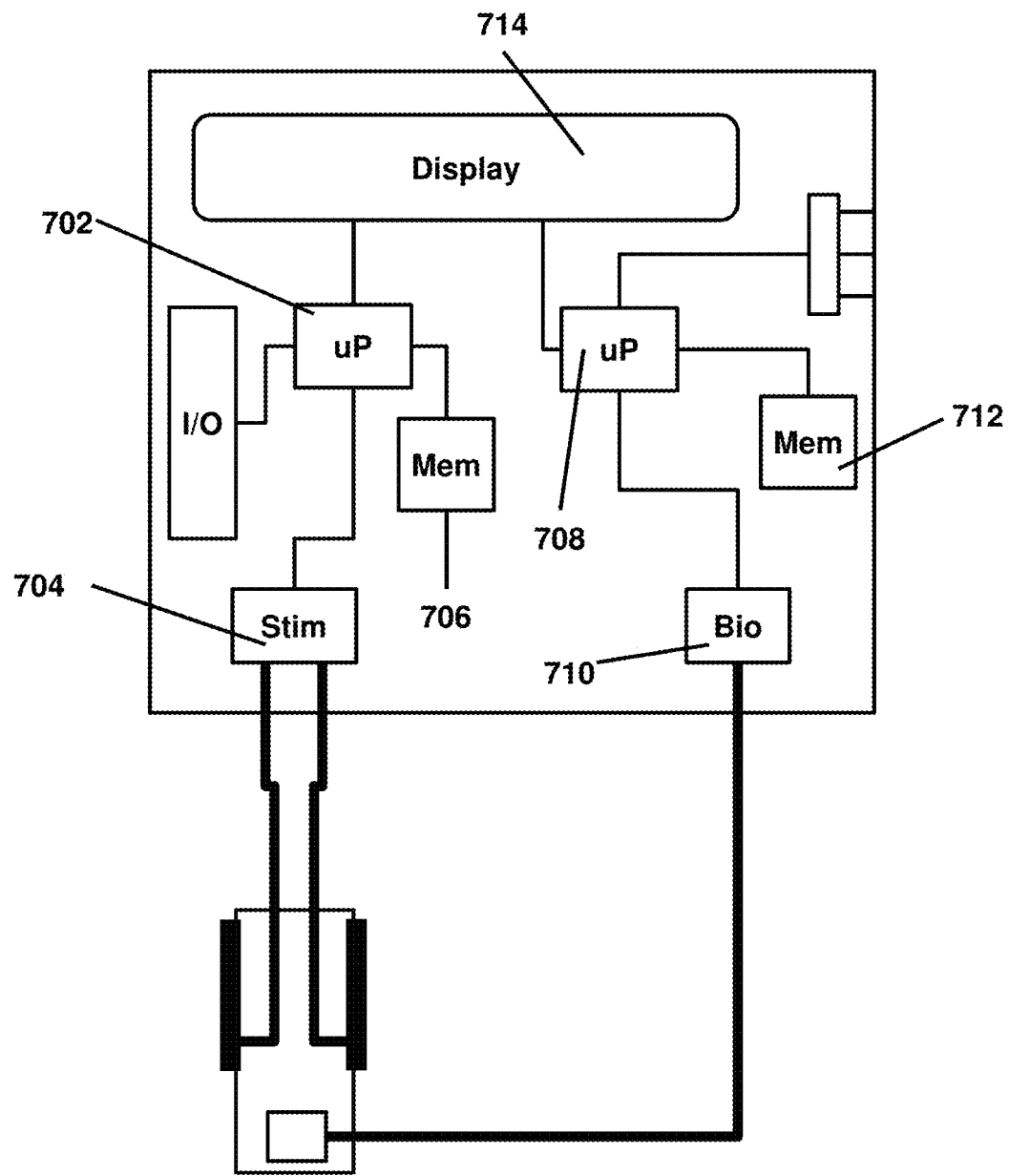
FIG. 7 is a simplified block diagram of another exemplary muscle stimulation device.

In other embodiments of the invention, a physical separation (firewall) between the stimulation portion and the biofeedback portion may be implemented. Such an embodiment is illustrated in FIG. 7. In such an embodiment, a first processor 702 may be in electrical communication with a stimulation portion 704. Software instructions may be contained in a memory 706 that is in electronic communication with the first processor 702. As illustrated, a second processor 708 may be in electronic communication with a biofeedback receiver 710 and a second memory 712. In such a configuration, an embodiment of the invention may have two isolated control sections such that there is a separation between the stimulation and biofeedback portions of the invention. Such a separation may further ensure that there is no undesired interaction between the stimulation and biofeedback portion of the invention. As illustrated, in embodiments of the invention, certain components such as a display portion 714 may be in communication with both the first processor 702 and the second processor 708 while retaining the isolation between the stimulation and biofeedback portions of the invention.

Figure 8:
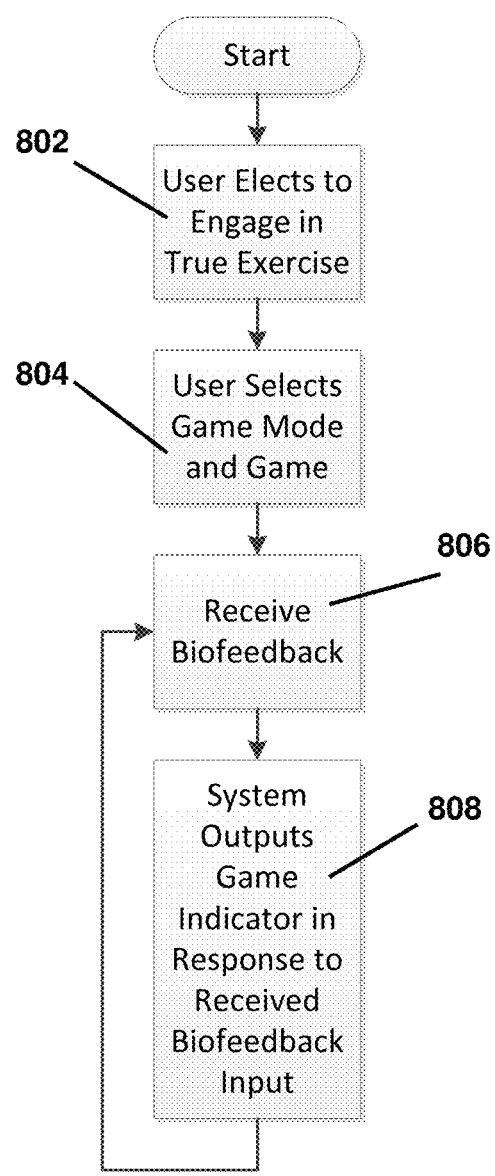
FIG. 8 is a flowchart of an exemplary method for interacting with the device in order to engage in a biofeedback game.

When the user desires to switch from stimulation to true exercise as defined herein, that user may elect to interact solely with the biofeedback portion of the invention. Referring again to the flowchart of FIG. 4, a user may select a biofeedback only operation 404. As illustrated, an embodiment of the invention may then receive biofeedback input data from the biofeedback receiver 110 in step 406. In certain embodiments of the invention, biofeedback results may be displayed to a user 408 in order to guide that user's performance of a series of exercise steps. As shown in the flowchart of FIG. 8, a user may elect to engage in true exercise 802. In step 804, such a user may select an exercise game from one or more such exercise games provided by an embodiment of the invention. During the process of a user's playing such a game, an embodiment of the invention may receive biofeedback data from the biofeedback receiver 102 in step 806. In order to provide feedback to a user, an embodiment of the invention may display a game indicator in response to the received input in step 808.

As with many forms of exercise, keeping the person performing the exercise engaged with the exercise may be facilitated by the use of games or similar competitive tasks. In such methods, providing a user the ability to compete against a series of predetermined tasks or alternatively, against another person, may distract the focus of such a person of the exercise itself and onto the competitive challenge provided by the game. Using such a technique, a user may find it easier and less tedious to perform the desired exercise. In embodiments of the present invention, the exercise goal is to encourage the user to perform a series of muscle contractions and releases of sufficient duration and intensity to produce an improvement in the muscle condition of the pelvic floor muscles of the person performing the exercise. As illustrated in FIG. 6, a user may be presented with a selection of various games 610. In the illustrated embodiment, the selection of games is intended to provide a series of exercise steps directed towards a specific goal. As illustrated, a first game 612 may involve encouraging a user to contract and release their muscles in a specific pattern. In the illustrated example, this is accomplished by displaying a bird 614 that appears to fly through the air. The bird can be made to rise and fall according to the biofeedback received by an embodiment of the invention. In such an embodiment, a rise of the displayed bird 614 may represent a user's increase in the strength of their muscle contraction. Conversely, the bird 614 may fall in response to the user's relaxing their muscles. As the bird 614 appears to fly through the air, a series of obstacles may be presented such that the user must contract their muscles to prevent the bird from colliding with the presented obstacle. Thus, to encourage the user to repeatedly contract their muscles, the series of obstacles 616 (illustrated as trees) may be presented in series according to how long it is desired to require the user to tighten their muscles. Similarly, in order to get the user to relax or vary the strength of the contraction of their muscles, a series of objects or prizes may be displayed 618 (here illustrated as pineapple shapes). Such prizes may be positioned at various levels of the display to encourage a user to maintain a predetermined level of contraction in order to cause the bird shape to pass over the prize.

As illustrated at 620, in other embodiments of the game a user may be encouraged to tighten their muscles to cause a displayed character to rise or fall along an incline as illustrated 622. As shown, the incline may be illustrated as an increasingly steep hill. The user may be encouraged to tighten or relax their muscles to cause the character to move up and down the incline or to hold the character in a certain position. These movements may cause the user to be aware of their ability to partially contract or relax their muscles. Similarly, in another embodiment of such a game, a user may be presented with a shape which can illustrate a contracted or relaxed muscle. As illustrated in FIG. 6 at 624, a flower may be shown as closed when a user's muscles are contracted or open 626 when that same user is causing their muscles to relax.

Figure 9:
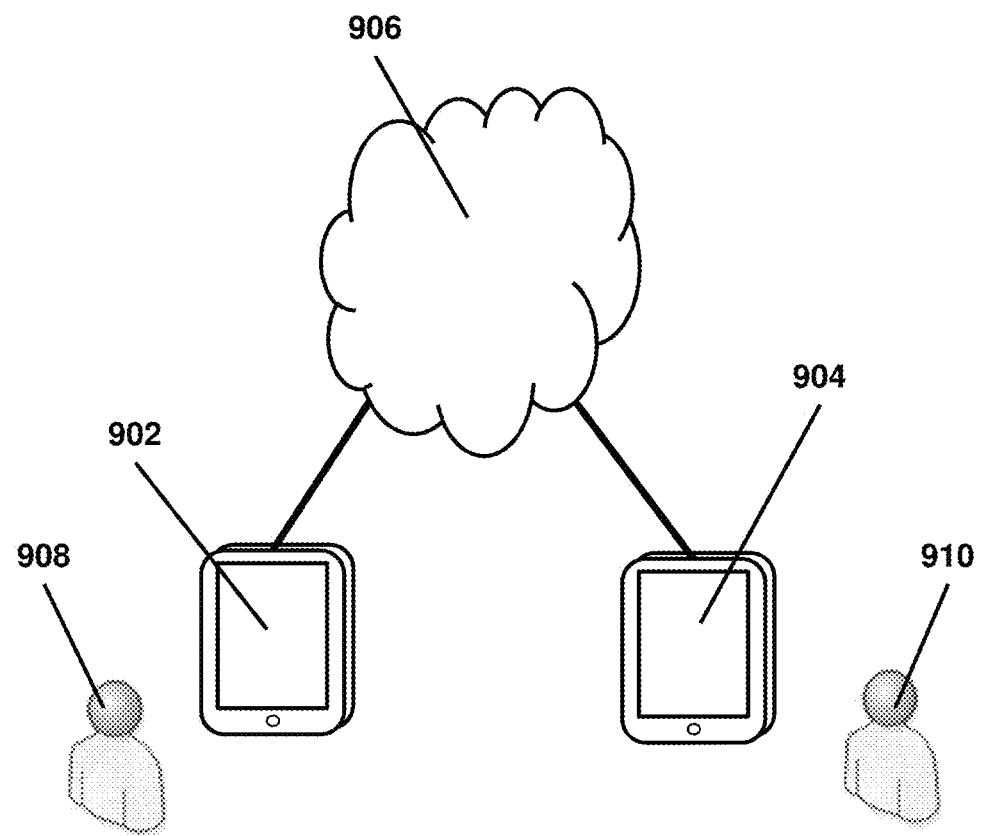
FIG. 9 is a simplified diagram of a system which permits users of devices to compete against each other.

In order to further engage a user, embodiments of the invention may be configured to communicate with other users as illustrated in FIG. 9. As shown, a first device 902 may be placed in electronic communication with a second device 904. As illustrated, the connections are formed using a connection through the internet 906. One ordinarily skilled in the art will understand that the connection from the devices 902 and 904 may involve Wi-Fi, a wired connection, cellular data or other connection methods that may become available. When connected, the user of the first device 908 and the user of the second device 910 may engage in a competitive game play mode in which the first and second user may compete against each other by performing contraction and relaxation movements such that they earn points or progress through a game more quickly than the other player in order to win the competitive game. As with single user game play modes, this embodiment of the invention may serve to further encourage a user to perform conditioning exercises in order to improve their muscle condition to prevent or improve conditions such as incontinence.

Figure 10:
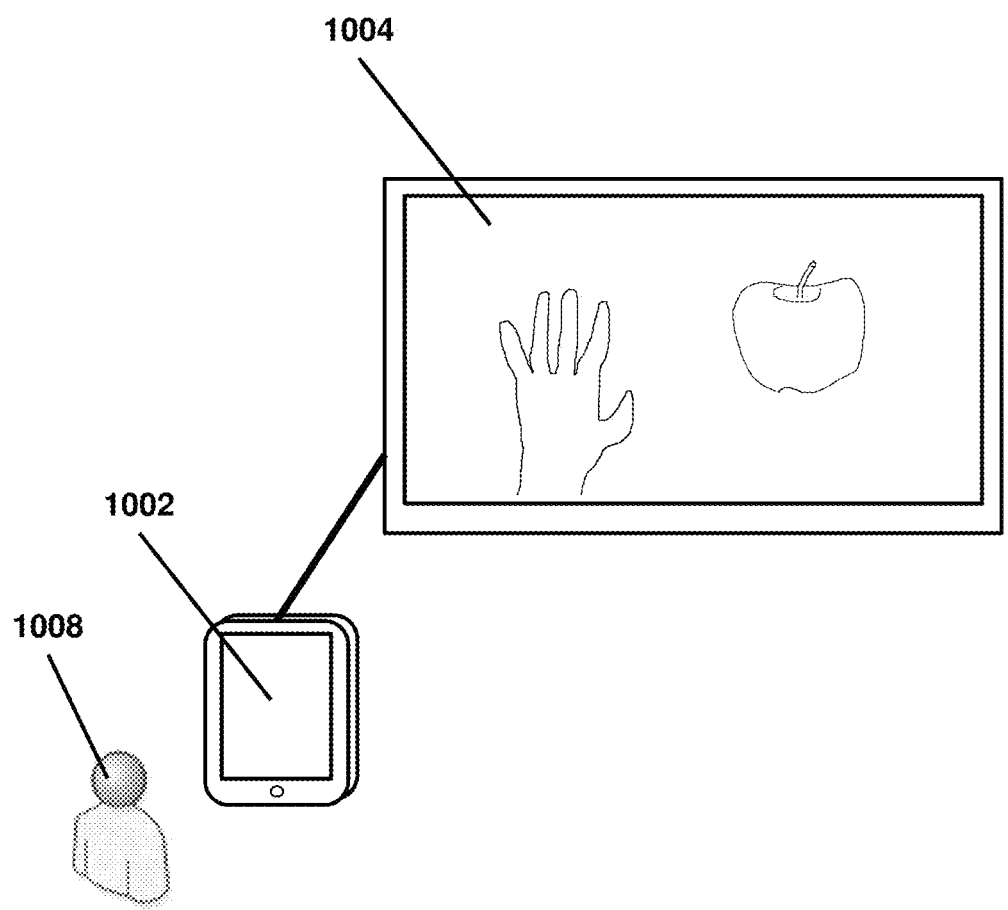
FIG. 10 is a simplified diagram of a visualization tool for the device.
Figure 11:
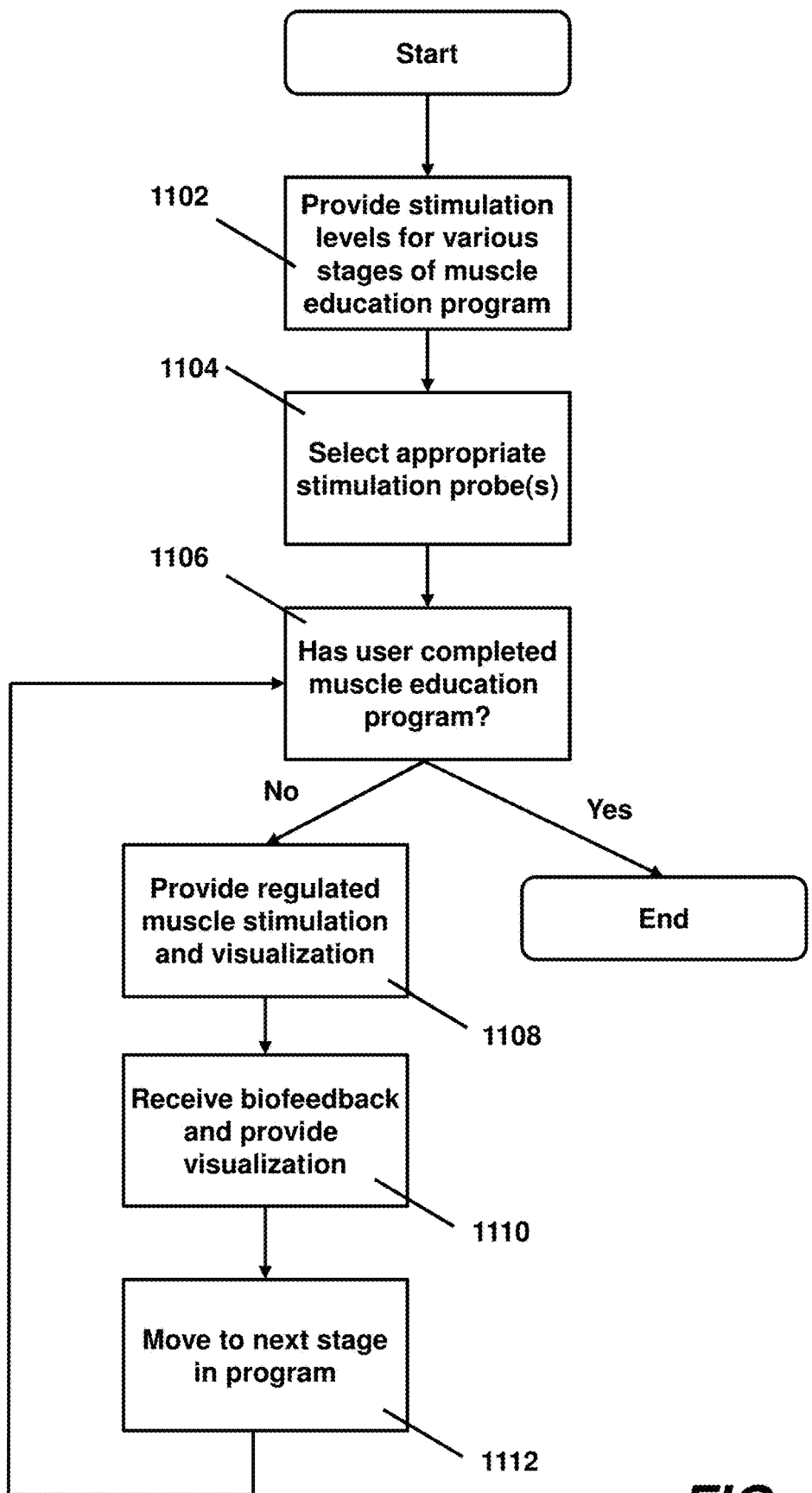
FIG. 11 is a flowchart illustrating exemplary logic for the system of FIG. 10.

FIG. 10 illustrates an exemplary embodiment with a device 1002 in electrical connection with a visualization tool 1004. FIG. 11 illustrates exemplary logic for use with the device 1002 and visualization tool 1004 of FIG. 10. At step 1102, various stimulation levels may be provided for various stages of a muscle education program. Such stimulation levels and stages of the muscle reeducation program may be prescribed, provided in text, chart, or the like. Alternatively, or in addition, such stimulation levels and stages of the muscle reeducation program may be programmed into the device 1002. The muscle stimulation may be selected to reflect a desired outcome. For example, without limitation, the desired outcome may be gripping a hand, moving a finger, extending a leg, standing up, or the like. Too much muscle stimulation may be counter-productive as it may result in regression of muscle education. Too little muscle stimulation may not adequately educate the muscles.

For each individual user the maximum therapeutic efficacy may be achieved, for example without limitation, by way of an algorithmic demonstration of sufficient muscle performance and respiration. Salient to the multi-variable algorithm is the status of the targeted muscle tissues including, but not limited to muscle responsiveness to following the requisite task and a determination of blood flow. Such characteristics may be measured and used to develop a regulated stimulation level specific to the patient and the desired muscle education. If the muscle is unable to perform specific template driven low level contraction challenges and/or exhibits any indications of spasm as monitored by an EMG then the next stimulation (NMES) cycle is blocked and remains arrested for as long as the muscle or muscle group cannot perform the threshold point prequalification parameters. As such, the provided stimulation may be selected based on characteristics of the specific individual user.

Alternatively, or in addition, the provided stimulation may be selected based on the user's condition or injury. In exemplary embodiments, the programmed stimulation levels may be selected to reflect clinical research, best practices, and the like regarding appropriate stimulation levels. Alternatively, or in addition, the device 1002 may be programmed with a number of predetermined stimulation levels associated with various user characteristics and/or injuries or conditions. The user may be prompted with questions to determine the user's characteristics and injury or condition and the device 1002 may suggest or select the associated predetermined stimulation level. Such predetermined stimulation levels may be stored at the memory 704, though such is not required. Regardless, the device 1002 may be regulated to only permit stimulation consistent with the provided stimulation levels for the given stage of the muscle education program.

At step 1104, the device 1002 may be fitted with one or more probes appropriate for the muscle group to be stimulated. For example, without limitation, the probes may be a slender wand, a pad, a sticker, some combination thereof, or the like. The probes may be provided in any number of sizes and shapes.

At step 1106, the device 1002 may determine which stage of the muscle education program the user is at and proceed accordingly. If the program is complete, the session may be ended. Otherwise, at step 1108, the device 1002 may begin with the initial stage and provide regulated muscle stimulation at the device 1002. The device 1002 may simultaneously display a visualization at the visualization tool 1004 at step 1008, though such is not required. The visualization may be of a particular activity and/or the desired outcome. For example, without limitation, the visualization device 1004 may display the image of a hand grasping an apple, a leg kicking a soccer ball, a person standing up, or the like. In this way, the user may associate the stimulation provided with the desired outcome to improve the muscle memory and likelihood that the neural pathways will be educated as desired.

At step 1110, biofeedback may be received at the device 1002. The device 1002 may simultaneously display a visualization at the visualization tool 1004 at step 1110, though such is not required. The visualization may reflect the biofeedback received in view of the desired outcome. For example, without limitation, the visualization device 1004 may display the image of a hand grasping an apple, a leg kicking a soccer ball, a person standing up, or the like consistent with the level of biofeedback received. For example, without limitation, the hand may only be partially contracted, the leg may only be partially extended (or the ball may only travel so far), or the person may only stand up enough to reflect the level of biofeedback received. If the user adequately contracts or relaxes the muscle group, the desired outcome may be displayed. If the user does not adequately contract or relax the muscle group, something less or different from the desired outcome may be displayed. In this way, the user is provided with a visual depiction of their progress towards the desired outcome. Furthermore, the visualization tool may serve as a gamification tool for improving the likelihood that the user will complete the muscle education program. Further still, the user may associate the muscular action with the depicted outcome to improve the muscle memory and likelihood that the neural pathways will be educated as desired. As each stage of the program is completed, at step 1112, the program may be advanced to the next stage.

In some embodiments, the visualization may be provided only with the biofeedback at step 1110. In other embodiments, the visualization may be provided only with the stimulation at step 1108. In still other embodiments, the visualization may be provided with both the stimulation at the feedback at steps 1108 and 1110. In still other embodiments, no visualization may be provided.

The visualization tool 1004 may be one or more electronic displays. The device 1002 and/or the visualization tool 1004 may be configured to display a visualization of the desired outcome. The visualization tool 1004 may be separate from, or integrated with, the device 1002. The visualization tool 1004 may be provided on a phone, tablet, computer, or the like. The visualization tool 1004 may be connected to the device 1002 by way of a wired or wireless connection.

Figure 12:
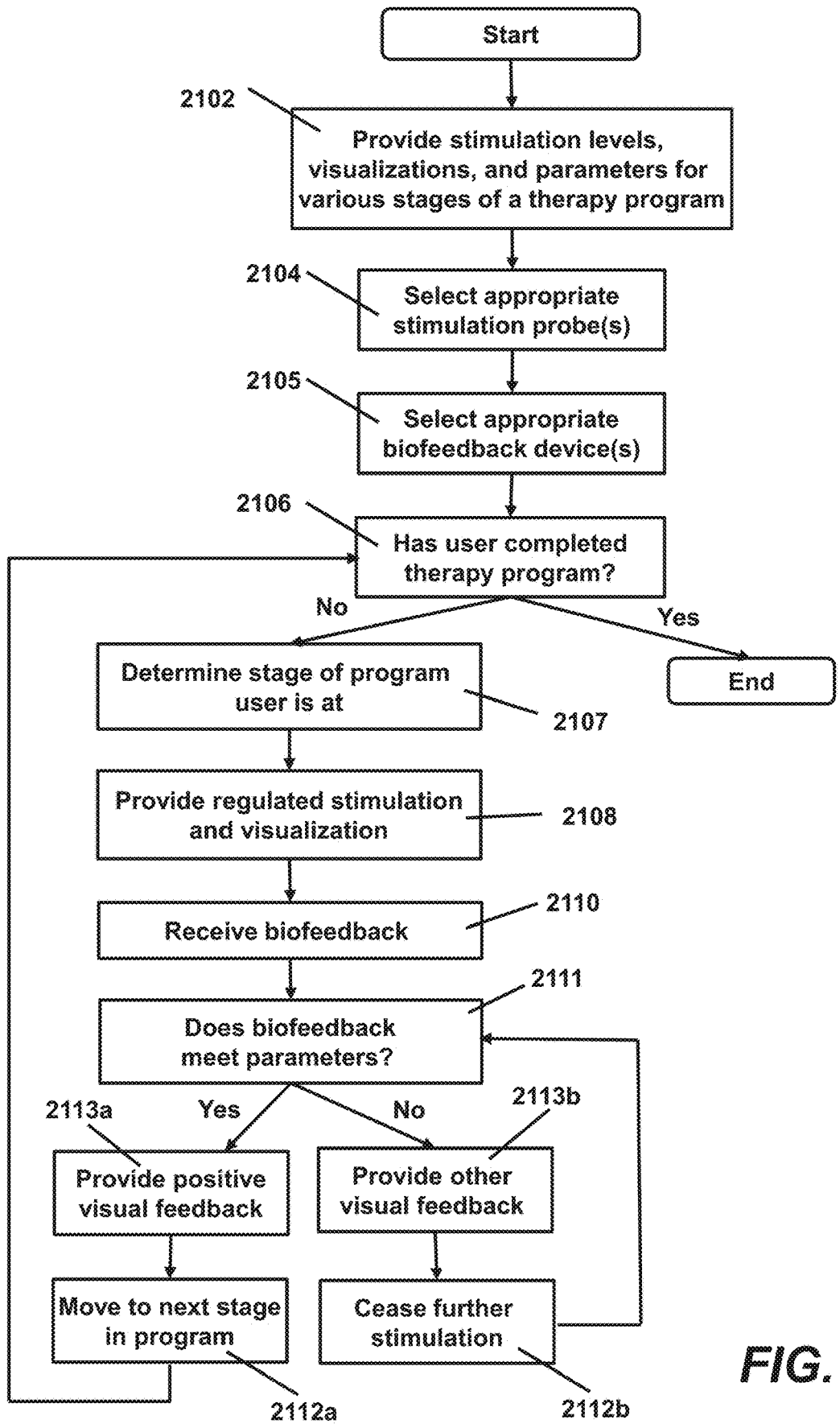
FIG. 12 is another flowchart illustrating exemplary logic for the system of FIG. 10.

FIG. 12 illustrates exemplary logic for use with the device 1002 and visualization tool 1004 of FIG. 10 or other devices shown and described herein. The logic illustrated in FIG. 12 may be used in addition to, or alternatively to, other exemplary logic shown or described herein. Similar steps may be numbered similarly but increased by 100 (e.g., 1102 to 1202). Stimulation levels, visualizations, and/or parameters may be received for each of a number of stages of a therapy program at step 2102. Appropriate stimulation devices(s) 104, 106 may be selected at step 2104. Appropriate biofeedback device(s) 110, 111 may be selected at step 2105. For example, without limitation, the biofeedback device 110, 111 may be selected for use with a particular body part matching the body part selected for use with the stimulation device 104, 106 at step 1104.

If the user has completed the therapy program at step 2106, the process may end. If the user has not completed the therapy program, the user's current stage of the program may be determined at step 2107. Regulated muscle stimulation and/or visualizations may be provided at step 2108 consistent with the stage of the program the user is at. The stimulation administered at step 2108 may be regulated in terms of wattage, voltage, amperage, time, frequency, duration, intensity, power, energy, some combination thereof, or the like. Biofeedback may be received at step 2110. After receiving such biofeedback at step 2110, a determination may be made as to whether the received biofeedback meets certain parameters at step 2111.

The parameters may be predetermined. The parameters may comprise thresholds, targets, ranges, some combination thereof, or the like. The parameters may be configured to reflect expected biofeedback matching the provided regulated muscle stimulation or visualization provided at step 2108. For example, without limitation, the regulated muscle stimulation may be provided at step 2108 to mimic action potentials provided by the central nervous system to mimic particular body part movements or other objects. The visualization provided at stem 2108 may reflect a certain desirable movement of the body part, for example without limitation, extending an arm or making a fist. The biofeedback collected may comprise muscle contraction and/or tension. The parameters may be selected to reflect the particular muscle movement mimicked in the regulated muscle stimulation and shown in the visualization with a margin of error.

Alternatively, or additionally, the regulated muscle stimulation may be provided at step 2108 to provide an analgesic effect to the user in exemplary embodiments, without limitation. The visualization may comprise a game. For example, without limitation, the visualization may comprise a game character, a game setting, and one or more objectives to be accomplished. The biofeedback collected may comprise muscle contraction, muscle tension, heart rate, blood flow, pain perception, blood pressure, some combination thereof, or the like. The parameters may be selected to reflect a relatively lowering of muscle contraction, muscle tension, heart rate, blood flow, pain perception, blood pressure, some combination thereof, or the like to reflect effective therapy.

Alternatively, or additionally, the visualization may be provided at step 2108 to engage and distract the user. For example, without limitation, pleasant images or video clips with motivational sayings, landscapes, music, some combination thereof, or the like may be provided.

If the biofeedback meets the parameters at step 2111, positive visual feedback may be provided at step 2113*a* and the user may be moved to the next stage in the therapy program provided at step 2112*a*. In this way, each stage may be completed sequentially until the entire program is completed. If the biofeedback does not meet the parameters at step 2111, other visual feedback may be provided at step 2113*b* and further stimulation may be discontinued at step 2112*b* until the proper biofeedback is received. This may act as a safety measure against overstimulation.

For example, without limitation, the positive visual feedback at step 2113*a* may comprise movement of the character through the game, completion of an objective, a positive message, desirable movement of a body part, movement of another object, new motivational sayings, new landscapes, some combination thereof, or the like. For example, without limitation, the other visual feedback at step 2113*b* may comprise lack of movement or regression of the character through the game, failure to complete an objective, a negative message, a message of encouragement, undesirable movement of a body part, undesired or lack of movement of another object, a lack of image change, some combination thereof, or the like.

Figure 13:
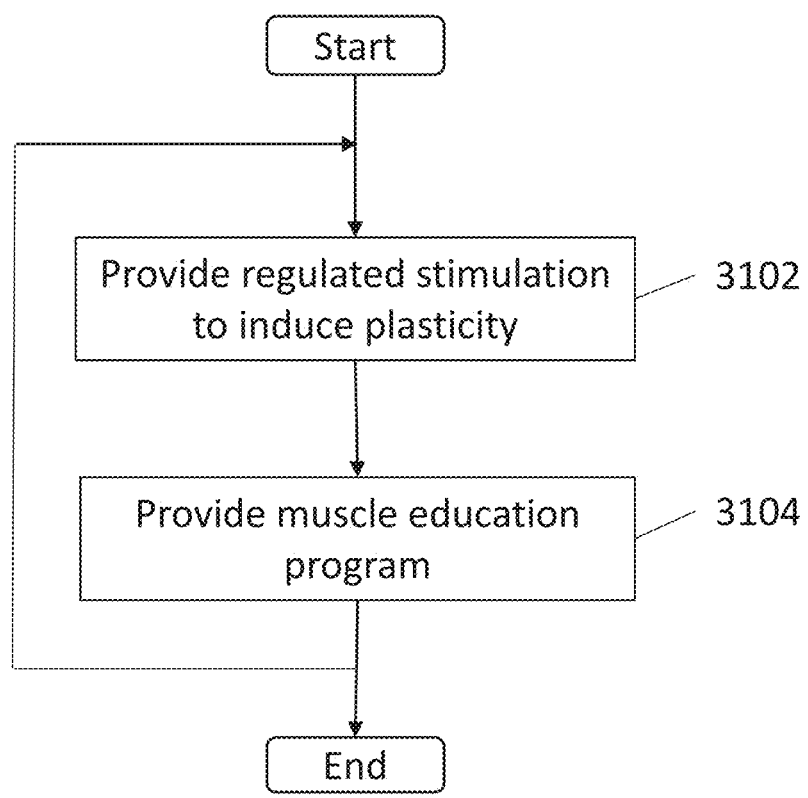
FIG. 13 is a flowchart illustrating exemplary logic for inducing a period of heightened plasticity.

FIG. 13 illustrates exemplary logic for forging neural pathways using a combination of regulated stimulation to induce a period of heightened plasticity at a user's brain and providing muscle education within the period of heightened plasticity. At step 3102, regulated stimulation may be provided to induce a period of heightened plasticity at the user's brain. In exemplary embodiments, this stimulation may be provided by the electrodes 106, such as but not limited to by way of the device shown and described with respect to FIG. 1 and/or FIG. 7. Additionally, or alternatively, such regulated stimulation may be provided by a separate stimulation device comprising one or more electrodes 106 connected to a stimulator 104 and one or more processors 102. Stated another way, such regulated stimulation may, in exemplary embodiments, be alternatively or additionally provided by a device similar or the same as the one shown and described with regard to FIGS. 1 and/or 7 but without the biofeedback portions. Regardless, the stimulation provided may be configured to induce stress in the user. The stress may cause the release of certain neurotransmitters which induce a period of heightened plasticity—the ability to learn and retain new information.

Following the regulated stimulation at step 3102, a muscle education program may be performed at step 3104. The muscle education program may preferably be performed immediately after completion of the regulated stimulation at step 3102, or as soon as practicable, such as the time it takes to remove any unneeded equipment, provide new equipment, set user parameters for the muscle education program, and the like. At a minimum, the muscle education program at step 3104 is performed during the period of heightened plasticity provided by the stimulation of step 3102, which may extend a certain number of minutes in exemplary embodiments. The muscle education program performed at step 3104 may include the automatic application of a multi-variable algorithm to induce and monitor targeted muscle performance and/or respiration to provide safe and efficacious therapy. The target muscles stimulated at step 3104 may be the same or different from those to which the stimulation to induce plasticity was applied at step 3102.

The muscle education program performed at step 3104 may comprise one or more of the techniques shown and/or described herein, such as with respect to at least FIGS. 2-6C, 8, 11-12, and/or 14. Alternatively, or additionally, the muscle education program performed at step 3104 may be performed using one or more of the devices shown and/or described herein, such as with respect to at least FIGS. 1, 7, and/or 9-10. In exemplary embodiments, the physical and/or electronic separation between the stimulation and biofeedback portions of devices used to provide the regulated stimulation and monitor for user muscle activity to provide feedback may provide safety against over stimulation, more accurate and precise stimulation, and more accurate and precise biofeedback.

The muscle education program performed at step 3104 may include visualizations of desired movements and/or regulated stimulation which induces such desired movements in exemplary embodiments. The induced actions themselves (by way of regulated stimulation and biofeedback) may forge new neural pathways and/or reinforce certain desirable existing neural pathways during the period of heightened plasticity where the user's brain is more likely to learn and retain the newly foraged and/or reinforced pathways. Alternatively, or additionally, the process of viewing desirable actions and/or being provided visual cues and/or feedback may forge new neural pathways and/or reinforce certain desirable existing neural pathways during the period of heightened plasticity where the user's brain is more likely to learn and retain the newly foraged and/or reinforced pathways.

Such feedback may, at least in part, satisfy the user's desire for novelty, divert focus from pain or other undesirable sensations, or otherwise provide an enjoyable experience to encourage further progress. The feedback may, alternatively or additionally, provide progress towards one or more objective goals. As the user accomplishes these goals, the user's pleasure centers of the brain may be stimulated. The accomplishment of tangible objectives over time may provide users with a sense of satisfaction that moves the user towards overcoming physical and/or emotional injury. In exemplary embodiments, such feedback may be provided intermittently, such as in an unpredictable fashion. Such unpredictability is not necessarily random, but may be provided at irregular intervals.

The process of performing regulated stimulation to induce plasticity at step 3102 and/or performing the muscle education program at step 3104 may be repeated periodically or continuously any number of times in conjunction with the same or different levels of stimulation at step 3102 and/or muscle education programs at step 3104, though such repetition is not required. For example, without limitation, the muscle education program may be repeated with increasing levels of tolerance between received biofeedback and desired biofeedback. As another example, without limitation, the muscle education program may be repeated with new desired actions requiring increasing levels of dexterity and/or coordination.

Exemplary applications of this approach include, but are not limited to, memory therapy (focus the attention of the user to a directed subject or task), speech therapy, immunotherapy (inducing natural immune responses), pain therapy (breathing control, association with positive visual cues), and sexual dysfunction. Such applications may be accomplished using visual and/or muscular cues. These are merely examples and are not intended to be limiting.

In exemplary embodiments, such applications may each have one or more corresponding objective goals. The goals may be specific to the patient, the therapy, the injury, the stimulation routine, combinations thereof, or the like. The goals may be structured for anticipated accomplishment over time. Such accomplishment may provide the user with a sense of satisfaction which may provide a therapeutic effect. For example, without limitation, the accomplishment of goals may provide an increased sense of self and/or wellbeing which may result in increased focus, reduced anxiety, reduced despair, combinations thereof, or the like. Examples of such objective goals include, but are not limited to, range of motion, reaction time, muscle contraction levels, combinations thereof, or the like.

Such goals may be programmed into the device, selected from preprogrammed goals, or the like. Such goals may be set to likely be accomplished at irregular intervals. The various steps shown and described herein may be performed in any order. Certain steps may be repeated or omitted.

Figure 14:
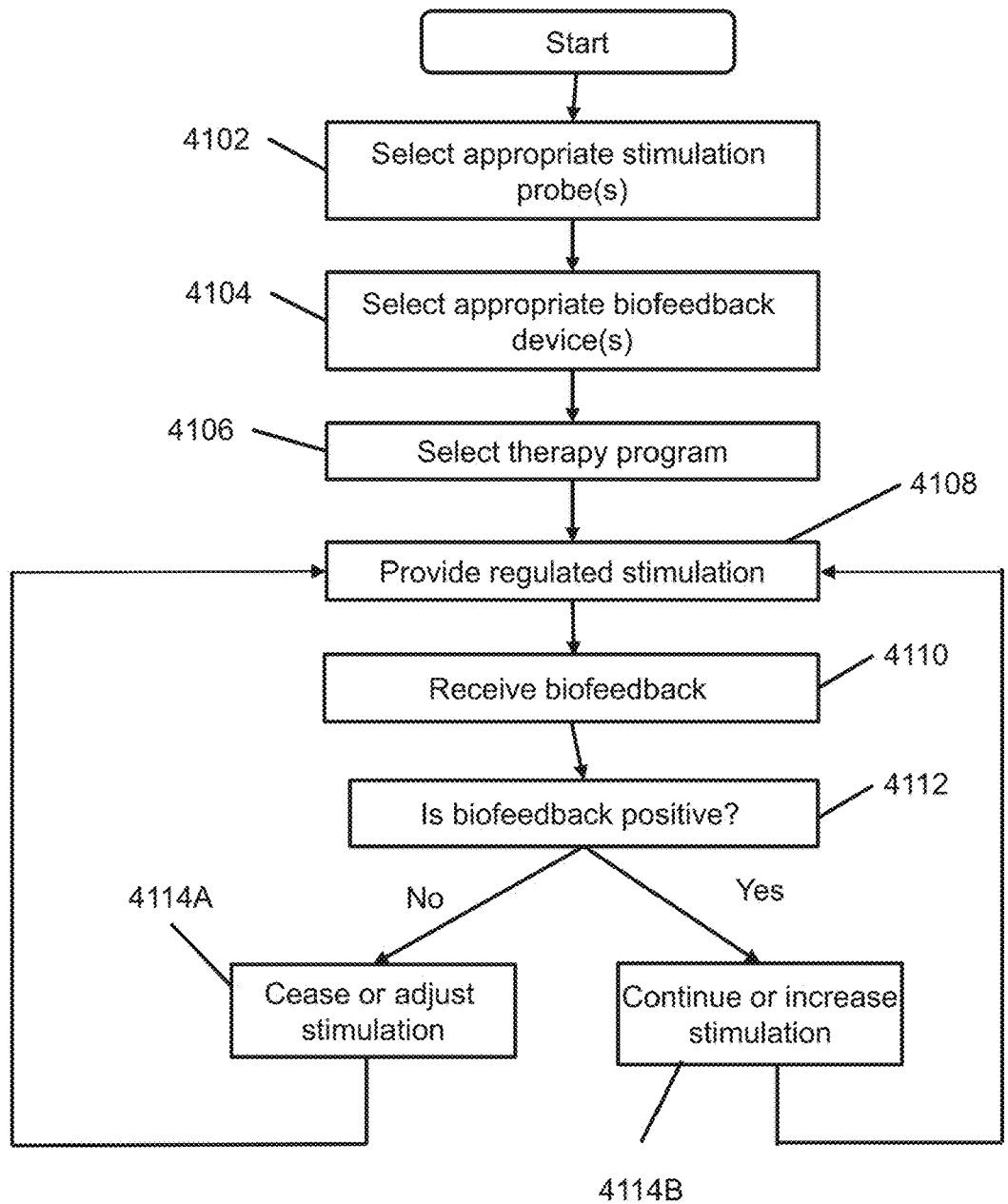
FIG. 14 is a flowchart illustrating exemplary logic for sensory regulated stimulation.

FIG. 14 illustrates exemplary logic for providing sensory regulated stimulation. This logic may provide feedback which may be used to, at least in part, control the stimulation such that muscles are not pushed beyond the therapeutic efficacy. Such feedback may be gathered, and stimulation adjusted, in substantially real-time, such as accounting for normal transmission and processing times. However, periodic or delayed updating may also be utilized. Such logic may be used with the devices shown and described herein. Such logic may be used in addition to, or alternatively to, other exemplary logic shown or described herein. One or more appropriate stimulation devices(s) 104, 106 may be selected at step 4102. One or more appropriate biofeedback device(s) 110, 111 may be selected at step 4104. For example, without limitation, the biofeedback device 110, 111 may be selected for use with a particular body part matching the body part selected for use with the stimulation device 104, 106 at step 4102.

Alternatively, or additionally, the biofeedback devices 110, 111 selected at step 4102 may include, for example without limitation, sensors configured to detect eye movements, facial expressions, and/or other muscle activity. Such movements may be detected by, for example without limitation, transducers, cameras, infrared sensors, retina trackers, pupil trackers, facial recognition software image recognition software, moisture detectors, pressure sensors, heart rate monitors, blood pressure detectors, oxygen saturation sensors, respiration monitors, combinations thereof, or other biofeedback sensor.

A therapy program may be selected at step 4106. The therapy program selected may include one or more predetermined stimulation levels, durations, intensities, combinations thereof, or the like. The therapy program selected may include one or more biofeedback goals, thresholds, parameters, combinations thereof, or the like. The therapy program may be specific to the patient, a body part, combinations thereof, or the like.

Regulated muscle stimulation may be provided at step 4108, and may be provided in a manner consistent with the selected therapy program. The stimulation administered at step 4108 may be regulated in terms of wattage, voltage, amperage, time, frequency, duration, intensity, power, energy, some combination thereof, or the like. Biofeedback may be received at step 4110. The biofeedback received at step 4110 may include, for example without limitation, eye movements, facial expressions, heart rate, blood pressure, respiration, combinations thereof, or other muscle activity.

After receiving such biofeedback at step 4110, a determination may be made at step 4112 as to whether the received biofeedback is positive or negative, such as by indicating a positive or negative user state. For example, without limitation, biofeedback received consistent with pain, stress, anxiety, combinations thereof, or the like may be determined to be negative. Biofeedback received consistent with pleasure, relief, focus, combinations thereof, or the like may be determined to be positive. Such biofeedback may include, for example without limitation, eye movement, pupil dilation, facial expressions, heart rate, muscle contraction, perspiration, respiration, blood pressure, oxygen saturation, shifting, combinations thereof, or muscle activity. In exemplary embodiments, a positive result may be determined where biofeedback is within predetermined thresholds, targets, ranges, some combination thereof, or the like. Similarly, a negative result may be determined where biofeedback is outside of predetermined thresholds, targets, ranges, some combination thereof, or the like.

Where a negative determination is made, at step 4114A stimulation may be ceased and/or adjusted, such as decreased in intensity, duration, frequency, combinations thereof, or the like. Where a positive determination is made, at step 4114B, stimulation may be continued and/or increase, such as increasing in intensity, duration, frequency, combinations thereof, or the like The logic of FIG. 14 may be used in conjunction with a visualization, such as but not limited to those shown and described with regard to FIGS. 10-12. Alternatively, or additionally, the logic of FIG. 14 may be used in conjunction with induced plasticity, such as but not limited to the logic shown and described with regard to FIG. 13. The stimulation provided and/or biofeedback received may be performed using one or more of the devices shown and/or described herein, such as with respect to at least FIGS. 1, 7, and/or 9-10.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose or specialized computing devices. The electronic devices may be personal computers, smartphones, tablets, databases, servers, or the like. The electronic connections described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A system for forging neural pathways, said system comprising:
   a controller comprising one or more electronic storage devices and one or more processors;
   one or more stimulation devices in electronic communication with said controller and configured to provide at least a first, second, third, and fourth regulated electrical stimulation to a muscle group at a portion of an individual's body when activated, where at least the second, third, and fourth regulated electrical stimulation are each configured to cause electrically stimulated muscular contractions of the muscle group consistent with a desired movement of said portion of the individual's body;
   one or more biofeedback devices in electronic communication with said controller and configured to measure activity of muscles at the individual's body; and
   executable software instructions stored at the one or more electronic storage devices of the controller which when executed configure the one or more processors to:
      provide the first regulated electrical stimulation to induce a period of heightened plasticity for the individual's brain;
      after providing the first regulated electrical stimulation, provide the second regulated electrical stimulation at the muscle group of the individual's body by way of the one or more stimulation devices;
      after providing the second regulated electrical stimulation, receive biofeedback from the one or more biofeedback devices;
      determine if said received biofeedback is positive or negative;
      only after positive biofeedback is received, provide the third regulated electrical stimulation which is increased relative to the second regulated electrical stimulation;
      where negative biofeedback is received, cease providing the second regulated electrical stimulation and instead provide the fourth regulated electrical stimulation which is decreased relative to the second regulated electrical stimulation;
      after providing the fourth regulated electrical stimulation, receive additional biofeedback from the one or more biofeedback devices;
      determine if said received additional biofeedback is positive or negative; and
      where negative biofeedback continues to be received, provide additional ones of the regulated electrical stimulation by way of the one or more stimulation devices at sequentially decreased levels down to a zero-stimulation level unless and until positive biofeedback is received following a respective one of the additional ones of the regulated electrical stimulation.

2. The system of claim 1 further comprising:
   an electronic display in electronic communication with said controller and configured to provide images of the desired movement of said portion of the individual's body; and
   additional executable software instructions stored at the one or more electronic storage devices of the controller which when executed configure the one or more processors to:
      provide the images of the desired movement of said portion of the individual's body at the electronic display;
      determine that said positive biofeedback is received where said received biofeedback aligns with said desired movement of said portion of the individual's body;
      provide positive feedback at said electronic display where the receipt of said positive biofeedback is determined;

determine that said negative biofeedback is received where said received biofeedback does not align with said desired movement of said portion of the individual's body; and provide negative feedback at said electronic display where the receipt of said negative biofeedback is determined.

3. The system of claim 2 wherein:

said positive feedback comprises images depicting completion of one or more goals of a game; and said negative feedback comprises images depicting failure of the one or more goals of the game.

4. The system of claim 2 wherein:

said positive feedback comprises images depicting a smiling face; and said negative feedback comprises images depicting a frowning face.

5. The system of claim 2 further comprising:

additional executable software instructions stored at the one or more electronic storage devices of the controller which when executed configure the one or more processors to display images depicting simulated movement of the portion of the individual's body at the electronic display consistent with the received biofeedback.

6. The system of claim 2 wherein:

said controller is configured to provide said images of the desired movement of said portion of the individual's body at the electronic display in synchronization with said second, third, and fourth regulated electrical stimulation.

7. The system of claim 1 wherein:

said controller is configured to provide said second, third, and fourth regulated electrical stimulation at the portion of the individual's body by way of the one or more stimulation devices to induce muscular contractions consistent with the desired movement of said portion of the individual's body during the period of heightened plasticity.

8. The system of claim 7 wherein:

said controller is configured to provide said second, third, and fourth regulated electrical stimulation at the portion of the individual's body by way of the one or more stimulation devices to induce muscular contractions consistent with the desired movement of said portion of the individual's body at least one additional time during the period of heightened plasticity.

9. The system of claim 1 wherein:

the one or more stimulation devices are configured to induce movement of muscles associated with speech; and the one or more biofeedback devices are configured to measure activity of the muscles associated with speech.

10. The system of claim 1 wherein:

the one or more stimulation devices are configured to induce movement of muscles associated with breath control; and the one or more stimulation devices are configured to measure activity of the muscles associated with breath control.

11. The system of claim 1 wherein:

each of said one or more stimulation devices are electrically isolated from each of said one or more biofeedback devices.

12. A system for forging neural pathways, said system comprising:

a controller comprising one or more electronic storage devices and one or more processors;

one or more stimulation devices in electronic communication with said controller and configured to provide at least a first, second, third, and fourth regulated electrical stimulation to a muscle group at a portion of an individual's body when activated, where at least the second, third, and fourth regulated electrical stimulation are each configured to cause electrically stimulated muscular contractions of the muscle group consistent with a desired movement of said portion of the individual's body;

one or more biofeedback devices in electronic communication with said controller and configured to measure activity of muscles at the individual's body, wherein at least one of said one or more biofeedback devices is configured to measure muscular activity of at least one of the individual's eyes;

an electronic display in electronic communication with said controller and configured to provides images of the desired movement of said portion of the individual's body;

a sound device in electronic communication with the controller and configured to electronically detect sounds; and executable software instructions stored at the one or more electronic storage devices of the controller which when executed configure the one or more processors to:

provide the first regulated electrical stimulation to induce a period of heightened plasticity for the individual's brain by way of the one or more stimulation devices;

after providing the first regulated electrical stimulation, provide the second regulated electrical stimulation at the muscle group by way of the one or more stimulation devices, where the second regulated electrical stimulation is initiated or altered based on the electronically detected sounds;

provide the images of the desired movement of said portion of the individual's body at the electronic display in synchronization with said second regulated electrical stimulation such that the images of said desired movement are provided at the same time as the second regulated stimulation;

monitor for biofeedback at said one or more biofeedback devices;

only after biofeedback consistent with pleasure or relief is received:

provide the third regulated electrical stimulation which is increased relative to the second regulated electrical stimulation; and provide a positive indication at said electronic display;

where biofeedback consistent with stress or pain is received, cease providing the second regulated electrical stimulation and instead provide the fourth regulated electrical stimulation which is decreased relative to the second regulated electrical stimulation;

after providing the fourth regulated electrical stimulation, receive additional biofeedback from the one or more biofeedback devices;

determine if said received additional biofeedback is consistent with pleasure or relief or stress or pain; and where biofeedback associated with stress or pain continues to be received, providing additional ones of the regulated electrical stimulation at sequentially decreased levels down to a zero-stimulation level unless and until positive biofeedback associated with pleasure or relief is received following a respective one of the additional ones of the regulated electrical stimulation.

\* \* \* \* \*